United States Patent
Dermatakis et al.

(10) Patent No.: US 6,531,598 B1
(45) Date of Patent: Mar. 11, 2003

(54) NAPHTHOSTYRILS

(75) Inventors: Apostolos Dermatakis, Edison, NJ (US); Jin-Jun Liu, Warren, NJ (US); Kin-Chun Luk, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/224,022

(22) Filed: Aug. 20, 2002

Related U.S. Application Data

(62) Division of application No. 10/043,732, filed on Jan. 10, 2002.
(60) Provisional application No. 60/263,658, filed on Jan. 23, 2001.

(51) Int. Cl.⁷ .................. C07D 413/14; C07D 401/14
(52) U.S. Cl. .................. 544/142; 546/200; 544/372
(58) Field of Search .................. 544/142; 546/276.7

(56) References Cited

U.S. PATENT DOCUMENTS

| | | | |
|---|---|---|---|
| 5,081,131 A | * 1/1992 | Tomcufcik et al. | ......... 514/339 |
| 5,206,261 A | 4/1993 | Kawaguchi et al. | |
| 5,750,556 A | * 5/1998 | Mewshaw et al. | ......... 514/411 |
| 6,130,239 A | 10/2000 | Chen et al. | |

FOREIGN PATENT DOCUMENTS

| | | |
|---|---|---|
| EP | 0 580 502 A1 | 1/1994 |
| WO | WO 92/07830 | 5/1992 |
| WO | WO 95/01349 | 1/1995 |
| WO | WO 96/16964 | 6/1996 |
| WO | WO 96/22976 | 8/1996 |
| WO | WO 96/32380 | 10/1996 |
| WO | WO 96/40116 | 12/1996 |
| WO | WO 97/07695 | 2/1998 |
| WO | WO 98/50356 | 11/1998 |

OTHER PUBLICATIONS

Abstract corresponding to EP 0 580 502 A1 (Document B1).

* cited by examiner

*Primary Examiner*—Joseph K. McKane
*Assistant Examiner*—Jennifer C. Murphy
(74) *Attorney, Agent, or Firm*—George W. Johnston; Patricia S. Rocha-Tramaloni

(57) ABSTRACT

Disclosed are novel naphthostyrils of formula

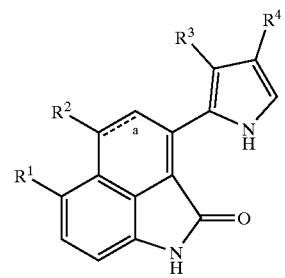

These compounds inhibit cyclin-dependent kinases (CDKs), in particular CDK2. These compounds and their pharmaceutically acceptable salts and esters are anti-proliferative agents useful in the treatment or control of cell proliferative disorders, in particular cancer. Also disclosed are pharmaceutical compositions containing such compounds, methods for the treatment and/or prevention of cancer using such compositions, and intermediates useful in the preparation of the compounds of formula I.

35 Claims, No Drawings

NAPHTHOSTYRILS

This application is a divisional application of U.S. Ser. No. 10/043,732, filed Jan. 10, 2002, which claims priority of Provisional Application Ser. No. 60/263,658, filed Jan. 23, 2001.

FIELD OF THE INVENTION

The present invention is directed to novel naphthostyrils of formula

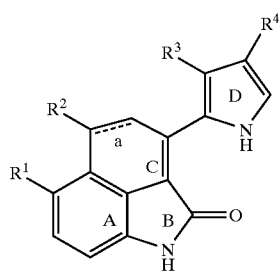

These compounds inhibit cyclin-dependent kinases (CDKs), in particular CDK2. These compounds and their pharmaceutically acceptable salts and esters are anti-proliferative agents useful in the treatment or control of cell proliferative disorders, in particular cancer. The invention is also directed to pharmaceutical compositions containing such compounds, and to methods for the treatment and/or prevention of cancer, particularly in the treatment or control of solid tumors. The compounds of the invention are especially useful in the treatment or control of breast, colon, lung and prostate tumors. The invention is also directed to intermediates useful in the preparation of the above antiproliferative agents.

BACKGROUND OF THE INVENTION

Uncontrolled cell proliferation is the hallmark of cancer. Cancerous tumor cells typically have some form of damage to the genes that directly or indirectly regulate the cell-division cycle.

Cyclin-dependent kinases (CDKs) are enzymes which are critical to cell cycle control. See, e.g., Coleman et al., "Chemical Inhibitors of Cyclin-dependent Kinases," *Annual Reports in Medicinal Chemistry*, vol. 32, 1997, pp. 171–179. These enzymes regulate the transitions between the different phases of the cell cycle, such as the progression from the $G_1$ phase to the S phase (the period of active DNA synthesis), or the progression from the $G_2$ phase to the M phase, in which active mitosis and cell-division occurs. See, e.g., the articles on this subject appearing in *Science*, vol. 274, Dec. 6, 1996, pp. 1643–1677.

CDKs are composed of a catalytic CDK subunit and a regulatory cyclin subunit. The cyclin subunit is the key regulator of CDK activity, with each CDK interacting with a specific subset of cyclins: e.g. cyclin A (CDK1, CDK 2). The different kinase/cyclin pairs regulate progression through specific stages of the cell cycle. See, e.g., Coleman, supra.

Aberrations in the cell cycle control system have been implicated in the uncontrolled growth of cancerous cells. See, e.g., Kamb, "Cell-Cycle Regulators and Cancer," *Trends in Genetics*, vol. 11, 1995, pp. 136–140; and Coleman, supra. In addition, changes in the expression of or in the genes encoding CDK's or their regulators have been observed in a number of tumors. See, e.g., Webster, "The Therapeutic Potential of Targeting the Cell Cycle," *Exp. Opin. Invest. Drugs,* Vol. 7, pp. 865–887 (1998), and references cited therein. Thus, there is an extensive body of literature validating the use of compounds inhibiting CDKs as anti-proliferative therapeutic agents. See, e.g. U.S. Pat. No. 5,621,082 to Xiong et al; EP 0 666 270 A2; WO 97/16447; and the references cited in Coleman, supra, in particular reference no. 10. Thus, it is desirable to identify chemical inhibitors of CDK activity.

It is particularly desirable to identify small molecule compounds that may be readily synthesized and are effective in inhibiting CDK2 or CDK2/cyclin complexes, for treating one or more types of tumors.

4-Alkenyl- and 4-alkynyloxindoles useful in the treatment or control of cancer are disclosed in U.S. Pat. No. 6,130,239. Indolinone (also known as oxindole) compounds asserted to be useful in regulating abnormal cell proliferation through tyrosine kinase inhibition are disclosed in WO 96/40116, WO 98/07695, WO 95/01349, WO 96/32380, WO 96/22976, WO 96/16964 (tyrosine kinase inhibitors), and WO 98/50356 (2-indolinone derivatives as modulators of protein kinase activity). Oxindole derivatives have also been described for various other therapeutic uses: 5,206,261 (improvement of cerebral function); WO 92/07830 (peptide antagonists); EP 580 502 A1 (antioxidants).

There continues to be a need for easily synthesized, small molecule compounds for the treatment of one or more types of tumors, in particular through regulation of CDKs. It is thus an object of this invention to provide such compounds and compositions containing such compounds.

SUMMARY OF THE INVENTION

The present invention relates to naphthostyrils capable of inhibiting the activity of one or more CDKs, in particular CDK2. These compounds are useful for the treatment or control of cancer, in particular solid tumors. In particular this invention is directed to a compound of the formula

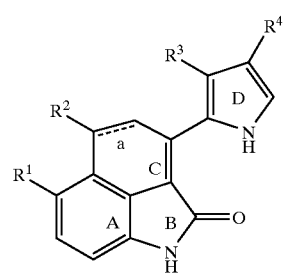

and the pharmaceutically acceptable salts and esters of such compound, wherein $R^1$–$R^4$ are as defined below.

The present invention is also directed to pharmaceutical compositions comprising a pharmaceutically effective amount of any one or more compounds of formula I and a pharmaceutically acceptable carrier or excipient.

The present invention is further directed to a method for treating solid tumors, in particular breast, colon, lung and prostate tumors, by administering to a human patient in need of such therapy an effective amount of a compound of formula I, its salt and/or ester or a combination thereof.

DETAILED DESCRIPTION OF THE INVENTION

Definitions

As used herein, the following terms shall have the following definitions.

"Aryl" means an aromatic group having 5 to 10 atoms and consisting of 1 or 2 rings. Examples of aryl groups include phenyl and 1- or 2-naphthyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of Formula I, or a pharmaceutically acceptable salt or ester thereof, that significantly inhibits proliferation and/or prevents differentiation of a human tumor cell, including human tumor cell lines, and is thus effective to prevent, alleviate or ameliorate symptoms of disease or prolong the survival of the subject being treated.

"Halogen" means fluorine, chlorine, bromine or iodine.

"Heteroaryl" groups are aromatic groups having 5 to 10 atoms, one or two rings, and containing one or more hetero atoms. Examples of heteroaryl groups include 2, 3 or 4-pyridyl, tetrazolyl, oxadiazolyl, pyrazinyl, quinolyl, pyrrolyl, and imidazolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom. Examples of heterocyclic compounds include pyrrolidinyl, tetrahydrofuranyl, morpholinyl, and the like.

"$IC_{50}$" refers to the concentration of a particular naphthostyril required to inhibit 50% of a specific measured activity. $IC_{50}$ can be measured, inter alia, as is described in Example 58, infra.

"Lower alkyl" denotes a straight-chain or branched saturated or unsaturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl, propenyl, propynyl, and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids ($R^{24}C(=O)OH$) are lower alkyl esters which may be substituted with $NR^{25}R^{26}$ where $R^{25}$ and $R^{26}$ are lower alkyl, or where $NR^{25}R^{26}$ taken together form a monocyclic aliphatic heterocycle, such as pyrrolidine, piperidine, morpholine, N-methylpiperazine, etc.; acyloxyalkyl esters of the formula $R^{24}C(=O)OCHR^{27}OC(=O)R^{28}$ where $R^{27}$ is hydrogen or methyl, and $R^{28}$ is lower alkyl or cycloalkyl; carbonate esters of the formula $R^{24}C(=O)OCHR^{27}OC(=O)OR^{29}$ where $R^{27}$ is hydrogen or methyl, and $R^{29}$ is lower alkyl or cycloalkyl; or aminocarbonylmethyl esters of the formula $R^{24}C(=O)OCH_2C(=O)NR^{25}R^{26}$ where $R^{25}$ and $R^{26}$ are hydrogen or lower alkyl, or where $NR^{25}R^{26}$ taken together form a monocyclic aliphatic heterocycle, such as pyrrolidine, piperidine, morpholine, N-methylpiperazine, etc.

Examples of lower alkyl esters are the methyl, ethyl, and n-propyl esters, and the like. Examples of lower alkyl esters substituted with $NR^{25}R^{26}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy)ethyl and 1-(cyclohexyloxycarbonyloxy)ethyl esters. Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, prodrug, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

The Compounds

In one embodiment, the invention is directed to a compound of formula:

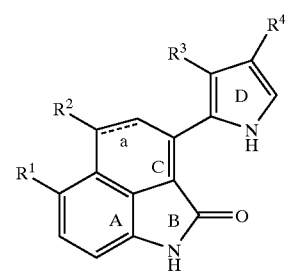

or the pharmaceutically acceptable salts or esters thereof, wherein:

$R^1$ is selected from the group consisting of
—H,
—$OR^5$,
halogen,
—CN,
—$NO_2$, —COR$^5$,
—COOR$^5$,
—CONR$^5$R$^6$,
—NR$^5$R$^6$,
—S(O)$_n$R$^5$,
—S(O)$_2$NR$^5$R$^6$, and
lower alkyl which optionally may be substituted by R$^7$;

R$^2$ is selected from the group consisting of
—H,
—OR$^5$,
halogen,
—CN,
—NO$_2$,
—COR$^5$,
—COOR$^5$,
—CONR$^5$R$^6$,
—NR$^5$R$^6$,
—S(O)$_n$R$^5$,
—S(O)$_2$NR$^5$R$^6$,
lower alkyl which optionally may be substituted by R$^7$,
cycloalkyl which optionally may be substituted by R$^8$, and
heterocycle which optionally may be substituted by R$^8$;

R$^3$ and R$^4$ are each independently selected from the group of
—H,
—OR$^5$,
—CN,
—NO$_2$,
—COR$^5$,
—COOR$^5$,
—CONR$^5$R$^6$,
—NR$^5$R$^6$,
—S(O)$_n$R$^5$,
—S(O)$_2$NR$^5$R$^6$, and
lower alkyl which optionally may be substituted by R$^7$;

R$^5$ is selected from the group consisting of
—H
lower alkyl which optionally may be substituted by R$^7$,
cycloalkyl which optionally may be substituted by R$^8$,
aryl which optionally may be substituted by R$^8$,
heteroaryl which optionally may be substituted by R$^8$, and
heterocycle which optionally may be substituted by R$^8$;

R$^6$ is selected from the group of
—H
—COR$^9$,
—CONR$^9$R$^{10}$,
—S(O)$_n$R$^9$,
—S(O)$_2$NR$^9$R$^{10}$,
lower alkyl which optionally may be substituted by R$^7$, and
cycloalkyl which optionally may be substituted by R$^8$,
or, alternatively, NR$^5$R$^6$ optionally may form a ring having 5–6 atoms, said ring optionally including one or more additional hetero atoms and being optionally substituted by R$^8$;

R$^7$ is selected from the group of
—OR$^9$,
halogen
—CN,
—NO$_2$,
—COR$^9$,
—COOR$^9$,
—CONR$^9$R$^{10}$,
—NR$^9$R$^{10}$,
—S(O)$_n$R$^9$,
—S(O)$_n$NR$^9$R$^{10}$;

R$^8$ is selected from the group of
—OR$^9$,
—CN,
—O,
—NO$_2$,
—COR$^9$,
—COOR$^9$,
—CONR$^9$R$^{10}$,
—NR$^9$R$^{10}$,
—S(O)$_n$R$^9$,
—S(O)$_2$NR$^9$R$^{10}$, and
lower alkyl which optionally may be substituted by R$^7$;

R$^9$ is selected from the group of
—H,
lower alkyl, and
cycloalkyl;

R$^{10}$ is selected from the group consisting of
—H,
—COR$^{11}$,
lower alkyl, and
cycloalkyl,
or, alternatively, NR$^9$R$^{10}$ optionally may form a ring having 5–6 atoms, said ring optionally including one or more additional hetero atoms;

R$^{11}$ is selected from the group consisting of lower alkyl, and
cycloalkyl;

a is an optional bond;

n is 0, 1 or 2; and

The letters A, B, C and D in formula I are merely for purposes of identifying each of the different rings in the formula.

In a preferred embodiment of the compounds of formula I, R$^1$ is selected from the group consisting of H, halogen, lower alkyl substituted by halogen, —NO$_2$, —CONR$^5$R$^6$, and —CN. The most preferred lower alkyls substituted by halogen include perfluoroalkyls. Preferred perfluoroalkyls include —CF$_3$. Preferred halogens include F.

In another preferred embodiment of the compounds of formula I, R$^2$ is selected from the group consisting of —H, —OR$^5$, NO$_2$, —CONR$^5$R$^6$, —S(O)$_n$R$^5$, —NR$^5$R$^6$, and lower alkyl which optionally may be substituted by R$^7$. Preferred —OR$^5$ groups include —OCH$_3$, —OCH$_2$CH$_3$, —OCH$_2$CH$_2$OH, —OCH$_2$CH$_2$CH$_2$OH, and —OCH$_2$CH$_2$NH$_2$. Preferred lower alkyls include perfluoroalkyl. Preferred perfluoroalkyls include —CF$_3$. Preferred —NR$^5$R$^6$ groups include —NHCH$_2$CH$_2$NH$_2$.

In another preferred embodiment of the compounds of formula I, R$^3$ and R$^4$ are selected from the group consisting of —H and lower alkyl which optionally may be substituted by R$^7$.

In another preferred embodiment of the compounds of formula I, R$^5$ is selected from the group consisting of lower alkyl which optionally may be substituted by R$^7$ and heterocycle which optionally may be substituted by R$^8$.

In another preferred embodiment of the compounds of formula I, R$^6$ is lower alkyl which optionally may be substituted by R$^7$.

In another preferred embodiment of the compounds of formula I, —NR$^5$R$^6$ is a ring having 5–6 atoms, said ring optionally including one or more additional hetero atoms and being optionally substituted by R$^8$.

In another preferred embodiment of the compounds of formula I, R$^7$ is selected from the group consisting of —OR$^9$ and —NR$^9$R$^{10}$.

In another preferred embodiment of the compounds of formula I, $R^8$ is selected from the group consisting of —OR$^9$ and —NR$^9$R$^{10}$.

In another preferred embodiment of the compounds of formula I, $R^9$ is selected from the group consisting of H and lower alkyl.

In another preferred embodiment of the compounds of formula I, $R^{10}$ is selected from the group consisting of H and lower alkyl.

In another preferred embodiment of the compounds of formula I, n is 0.

In another preferred embodiment of the compounds of formula I, "a" is a bond.

The following are examples of preferred compounds of formula I:

6-Fluoro-3-(1H-pyrrol-2-yl)-1H-benzo[cd]indol-2-one,
5-(2-Amino-ethylamino)-6-fluoro-3-(1H-pyrrol-2-yl)-1H-benzo[cd]indol-2-one,
5-(2-Amino-ethylamino)-6-fluoro-3-(1H-pyrrol-2-yl)-1H-benzo[cd]indol-2-one hydrochloride salt,
5-(2-Amino-ethylamino)-6-fluoro-3-(1H-pyrrol-2-yl)-1H-benzo[cd]indol-2-one methanesulfonic acid salt,
5-(2-Amino-ethylamino)-6-fluoro-3-(1H-pyrrol-2-yl)-1H-benzo[cd]indol-2-one trifluoroacetic acid salt,
6-Fluoro-5-methoxy-3-(1H-pyrrol-2-yl)-1H-benzo[cd]indol-2-one,
5-Ethoxy-6-fluoro-3-(1H-pyrrol-2-yl)-1H-benzo[cd]indol-2-one,
6-Fluoro-5-(2-hydroxy-ethylamino)-3-(1H-pyrrol-2-yl)-1H-benzo[cd]indol-2-one,
6-Fluoro-5-(2-hydroxy-ethoxy)-3-(1H-pyrrol-2-yl)-1H-benzo[cd]indol-2-one,
6-Fluoro-5-(3-hydroxy-propoxy)-3-(1H-pyrrol-2-yl)-1H-benzo[cd]indol-2-one,
5-(2-Amino-ethoxy)-6-fluoro-3-(1H-pyrrol-2-yl)-1H-benzo[cd]indol-2-one,
5-(2-Amino-ethoxy)-6-fluoro-3-(1H-pyrrol-2-yl)-1H-benzo[cd]indol-2-one methanesulfonic acid salt,
5-(3-Amino-propylamino)-6-fluoro-3-(1H-pyrrol-2-yl)-1H-benzo[cd]indol-2-one acetic acid salt,
5-(2-Amino-2-methyl-propylamino)-6-fluoro-3-(1H-pyrrol-2-yl)-1H-benzo[cd]indol-2-one,
6-Fluoro-5-morpholin-4-yl-3-(1H-pyrrol-2-yl)-1H-benzo[cd]indol-2-one,
6-Fluoro-5-piperazin-1-yl-3-(1H-pyrrol-2-yl)-1H-benzo[cd]indol-2-one acetic acid salt,
6-Fluoro-5-methyl-3-(1H-pyrrol-2-yl)-1H-benzo[cd]indol-2-one, (rac)-5-sec-Butyl-6-fluoro-3-(1H-pyrrol-2-yl)-1H-benzo[cd]indol-2-one,
5-Ethyl-6-fluoro-3-(1H-pyrrol-2-yl)-1H-benzo[cd]indol-2-one,
6-Fluoro-5-(2-oxo-imidazolidin-1-yl)-3-(1H-pyrrol-2-yl)-1H-benzo[cd]indol-2-one,
N-[2-[6-Fluoro-2-oxo-3-(1H-pyrrol-2-yl)-1,2-dihydro-benzo[cd]indol-5-ylamino]-ethyl]-acetamide,
5-(2-Dimethylamino-ethylamino)-6-fluoro-3-(1H-pyrrol-2-yl)-1H-benzo[cd]indol-2-one trifluoroacetic acid salt,
5-(2-Diethylamino-ethylamino)-6-fluoro-3-(1H-pyrrol-2-yl)-1H-benzo[cd]indol-2-one,
6-Fluoro-5-[(R)-3-hydroxy-pyrrolidin-1-yl)]-3-(1H-pyrrol-2-yl)-1H-benzo[cd]indol-2-one,
6-Fluoro-5-(4-hydroxy-piperidin-1-yl)-3-(1H-pyrrol-2-yl)-1H-benzo[cd]indol-2-one,
6-Fluoro-5-(3-hydroxymethyl-piperidin-1-yl)-3-(1H-pyrrol-2-yl)-1H-benzo[cd]indol-2-one,
6-Fluoro-5-(3-hydroxy-piperidin-1-yl)-3-(1H-pyrrol-2-yl)-1H-benzo[cd]indol-2-one,
6-Fluoro-5-(2-hydroxy-ethylsulfanyl)-3-(1H-pyrrol-2-yl)-1H-benzo[cd]indol-2-one,
6-Fluoro-5-(2-hydroxy-ethanesulfinyl)-3-(1H-pyrrol-2-yl)-1H-benzo[cd]indol-2-one,
6-Fluoro-5-(2-hydroxy-ethanesulfonyl)-3-(1H-pyrrol-2-yl)-1H-benzo[cd]indol-2-one,
5-(2-Amino-ethylsulfanyl)-6-fluoro-3-(1H-pyrrol-2-yl)-1H-benzo[cd]indol-2-one,
5-(2-Amino-ethylsulfanyl)-6-fluoro-3-(1H-pyrrol-2-yl)-1H-benzo[cd]indol-2-one hydrochloride salt,
5-(2-Amino-ethanesulfinyl)-6-fluoro-3-(1H-pyrrol-2-yl)-1H-benzo[cd]indol-2-one,
5-(2-Amino-ethanesulfinyl)-6-fluoro-3-(1H-pyrrol-2-yl)-1H-benzo[cd]indol-2-one hydrochloride salt,
5-(2-Amino-ethanesulfonyl)-6-fluoro-3-(1H-pyrrol-2-yl)-1H-benzo[cd]indol-2-one,
5-(2-Amino-ethylsulfanyl)-6-fluoro-3-(3,4-dimethyl-1H-pyrrol-2-yl)-1H-benzo[cd]indol-2-one trifluoroacetic acid salt,
6-Fluoro-5-(-(S)-pyrrolidin-2-ylmethylsulfanyl)-3-(1H-pyrrol-2-yl)-1H-benzo[cd]indol-2-one, and
6-Fluoro-5-[(S)-(pyrrolidin-3-ylsulfanyl)]-3-(1H-pyrrol-2-yl)-1H-benzo[cd]indol-2-one.

The compounds disclosed herein and covered by the above formulae may exhibit tautomerism, or structural or stereo isomerism. It is intended that the invention encompasses any tautomeric or structural or stereo isomeric form of these compounds, or mixtures of such forms, and is not limited to any one tautomeric or structural or stereo isomeric form utilized within the formulae drawn above.

General Synthesis of Compounds According to the Invention

The compounds of the invention may be prepared by processes known in the art. Suitable processes for synthesizing these compounds are provided in the examples. Generally, compounds of formula I may be prepared according to one of the below described synthetic routes.

Scheme 1:

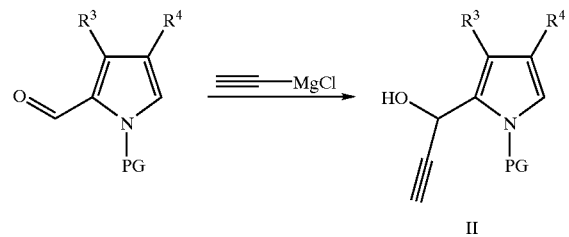

Where PG is a suitable protecting group such as tert-butoxycarbonyl.

Scheme 2:

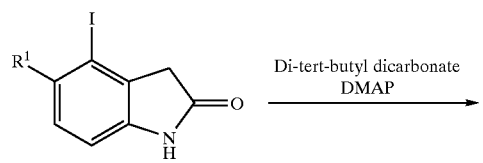

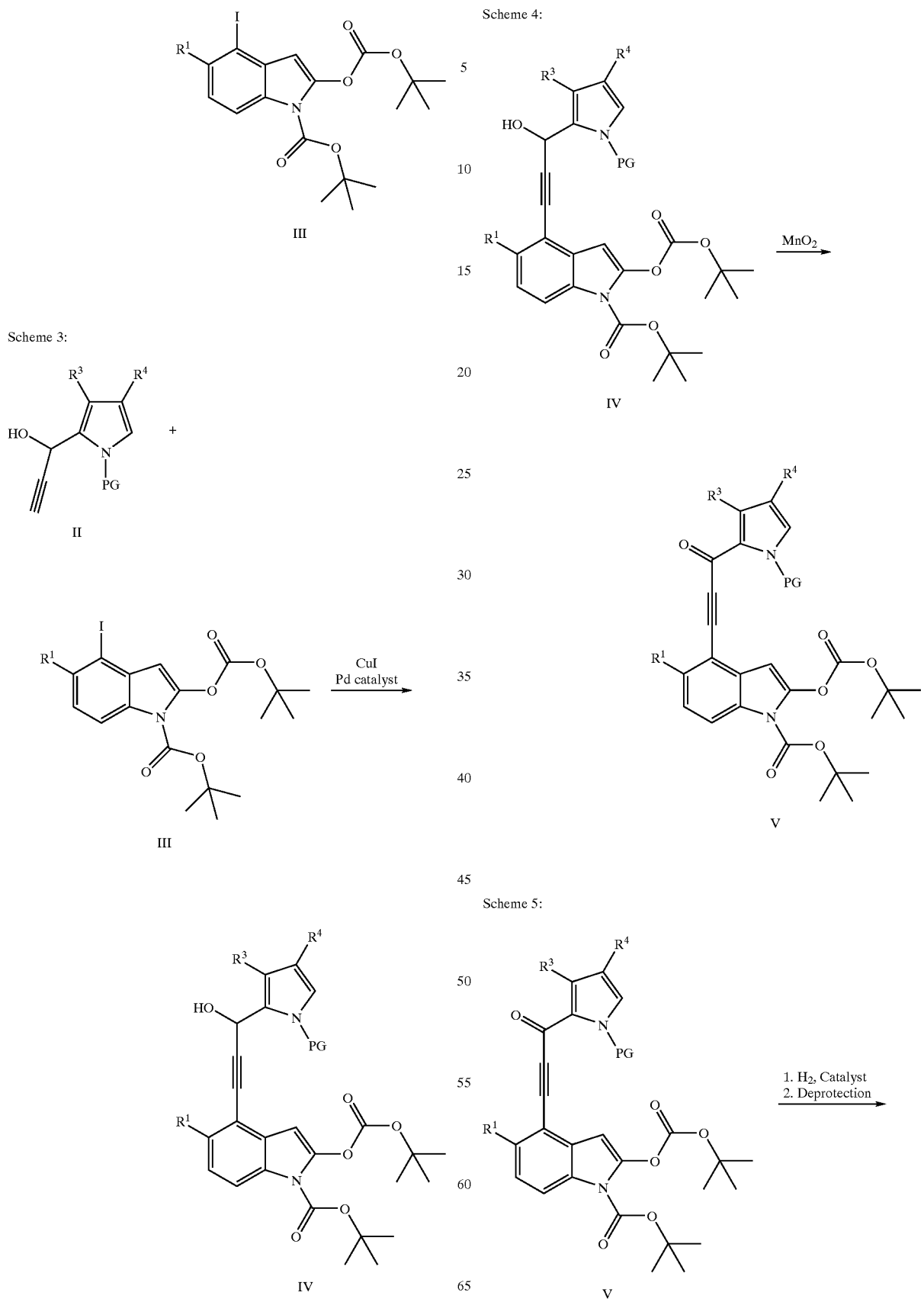

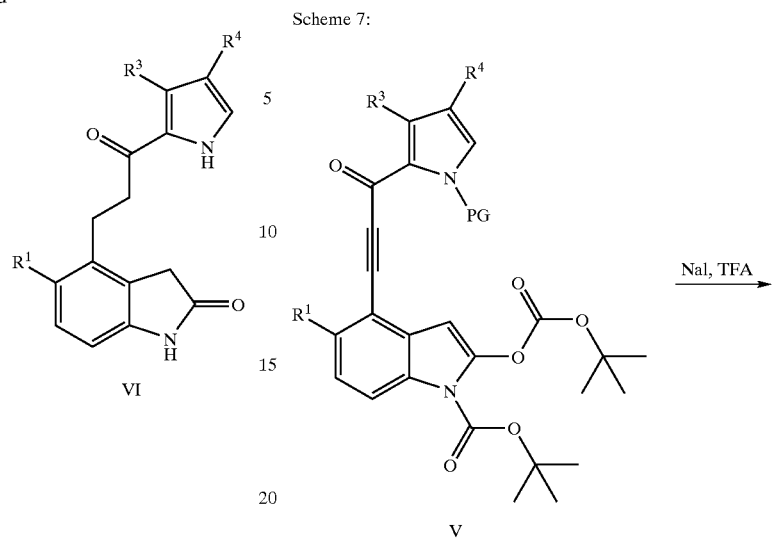
Where "deprotection" means using suitable methods well known in the art of chemical synthesis to remove protecting groups, such as treating with acid to remove the tert-butoxycarbonyl group.
Scheme 6:
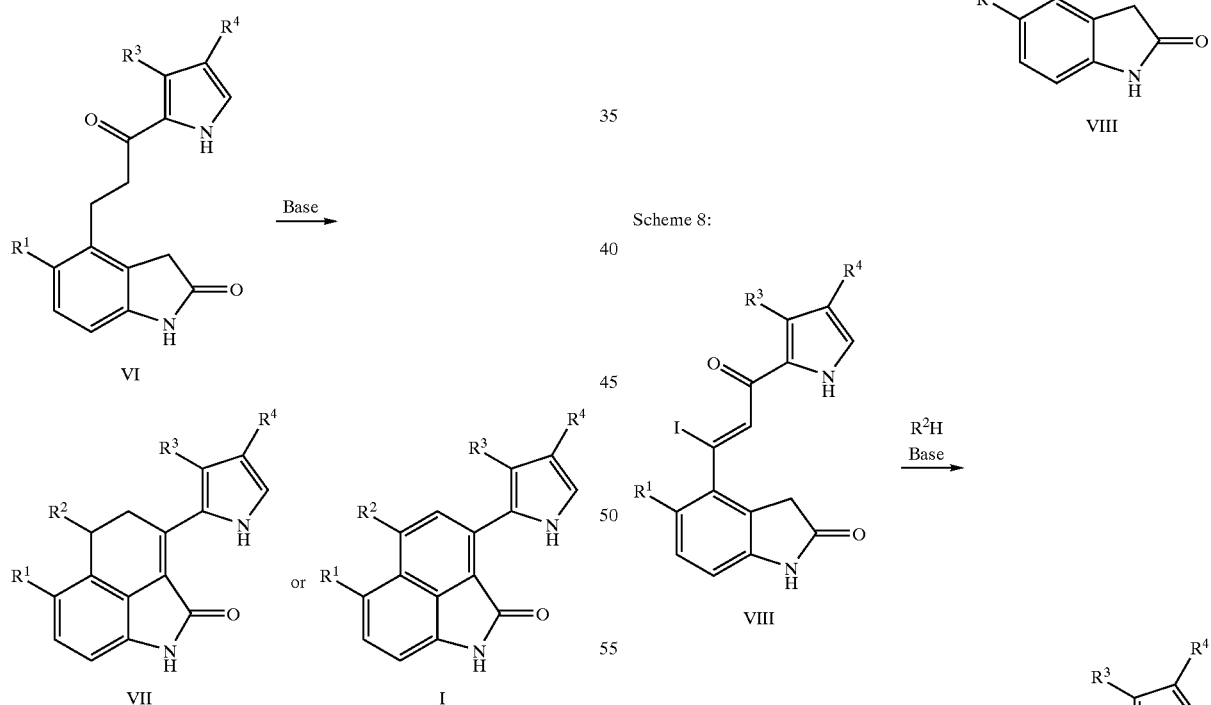
Preferred base includes 1 N sodium hydroxide, which upon heating in the presence of compound VI yields compound VII, and on prolonged heating, yields compound I.

Preferred base includes NaH.

Scheme 9:

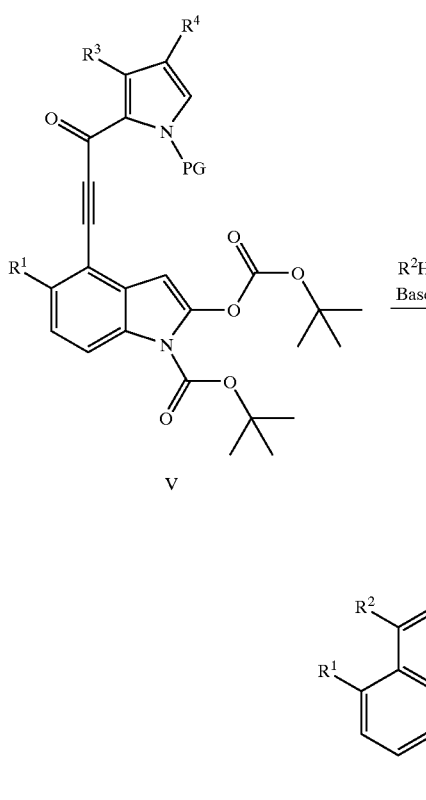

Scheme 10:

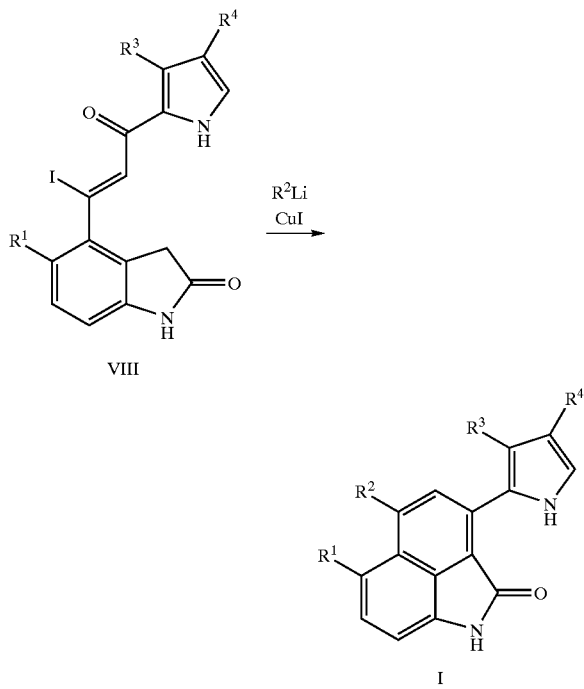

Formation of compound I can be acheived by using organo-cuprate reagents.

Scheme 11:

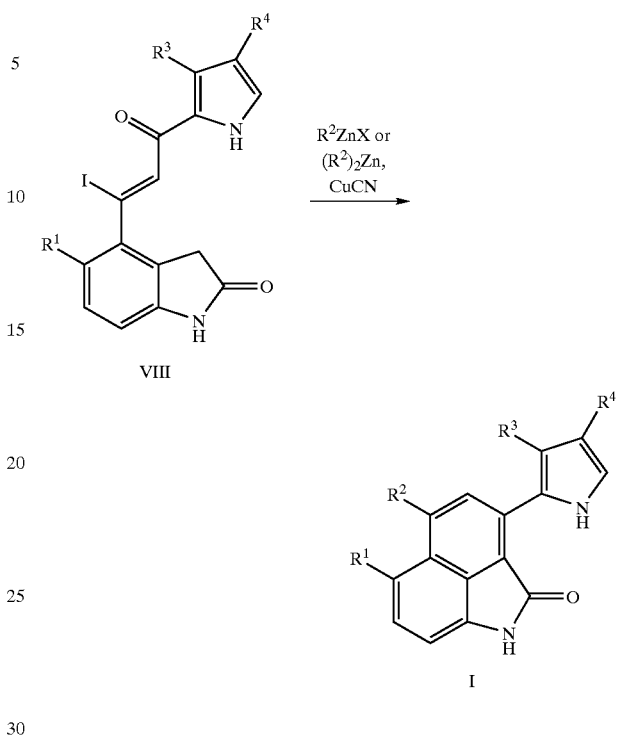

Formation of compound I can be achieved by using organo-zinc/copper reagents where X is Br or I.

Scheme 12

Compounds of Formula I can also be obtained by chemical modification of another compound of Formula I using chemical transformations well know in the art.

Compositions/Formulations

In an alternative embodiment, the present invention is directed to pharmaceutical compositions comprising at least one compound of formula I and/or a pharmaceutically acceptable salt or ester thereof.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising a compound of formula I and/or the salt or ester thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Novel Intermediates

In another embodiment, the present invention is also directed to novel intermediates useful in the preparation of compounds of formula I. These novel intermediates include the following compounds:

2-(1-Hydroxy-prop-2-ynyl)-pyrrole-1-carboxylic acid tert-butyl ester, 2-tert-Butoxycarbonyloxy-5-fluoro-4-iodo-indole-1-carboxylic acid tert-butyl ester, 2-tert-Butoxycarbonyloxy-4-[3-(1-tert-butoxycarbonyl-1H-pyrrol-2-yl)-3-hydroxyprop-1-ynyl]-5-fluoro-indole-1-carboxylic acid tert-butyl ester, 2-tert-Butoxycarbonyloxy-4-[3-(1-tert-butoxycarbonyl-1H-pyrrol-2-yl)-3-oxo-prop-1-ynyl]-5-fluoro-4-indole-1-carboxylic acid tert-butyl ester, 5-Fluoro-4-[3-oxo-3-(1H-pyrrol-2-yl)-propyl]-1,3-dihydro-indol-2-one, (Z)-5-Fluoro-4-[1-iodo-3-oxo-3-(1H-pyrrol-2-yl)-propenyl]-1,3-dihydro-indol-2-one,

[2-[6-Fluoro-2-oxo-3-(1H-pyrrol-2-yl)-1,2-dihydro-benzo[cd]indol-5-yloxy]-ethyl]-carbamic acid tert-butyl ester,

[2-[6-Fluoro-2-oxo-3-(1H-pyrrol-2-yl)-1,2-dihydro-benzo[cd]indol-5-ylsulfanyl]-ethyl]-carbamic acid tert-butyl ester, 3,4-Dimethyl-2-(1-hydroxy-prop-2-ynyl)-pyrrole-1-carboxylic acid tert-butyl ester, 2-tert-Butoxycarbonyloxy-4-[3-(1-tert-butoxycarbonyl-3,4-dimethyl-1H-pyrrol-2-yl)-3-hydroxy-prop-1-ynyl]-5-fluoro-indole-1-carboxylic acid tedt-butyl ester, 2-tedt-Butoxycarbonyloxy-4-[3-(1-tert-butoxycarbonyl-3,4-dimethyl-1H-pyrrol-2-yl)-3-oxo-prop-1-ynyl]-5-fluoro-indole-1-carboxylic acid tedt-butyl ester, 5-Fluoro-4-[1-iodo-3-oxo-3-(3,4-dimethyl-1H-pyrrol-2-yl)-propenyl]-1,3-dihydro-indol-2-one,

[2-[6-Fluoro-2-oxo-3-(3,4-dimethyl-1H-pyrrol-2-yl)-1,2-dihydro-benzo[cd]indol-5-ylsulfanyl]-ethyl]-carbamic acid tedt-butyl ester, 5-Fluoro-4-[3-oxo-3-(1H-pyrrol-2-yl)-propyl]-1,3-dihydro-indol-2-one, (±)-trans-Thioacetic acid-[3-(tert-butyl-dimethyl-silanyloxy)-cyclopentyl]ester, (±)-5-[trans-3-(tert-Butyl-dimethyl-silanyloxy)-cyclopentylsulfanyl]-6-fluoro-3-(1H-pyrrol-2-yl)-1H-benzo[cd]indol-2-one, and (S)-3-[6-Fluoro-2-oxo-3-(1H-pyrrol-2-yl)-1,2-dihydro-benzo[cd]indol-5-ylsulfanyl]-pyrrolidine-1-carboxylic acid tert-butyl ester.

EXAMPLES

The following examples illustrate preferred methods for synthesizing the compounds and formulations of the present invention. In the following examples, the below abbreviations are used:

ETOH=ethanol
THF=tetrahydrofuran
DMAP=4-dimethylaminopyridine
TFA=trifluoroacetic acid
DMF=N,N-dimethylformamide
MCPBA=meta-chloroperbenzoic acid Example 1

2-(1-Hydroxy-prop-2-ynyl)-pyrrole-1-carboxylic acid tert-butyl ester

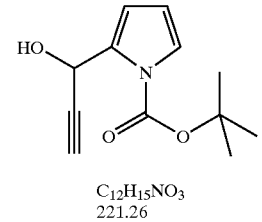

$C_{12}H_{15}NO_3$
221.26

To a solution of 2-formyl-pyrrole-1-carboxylic acid tert-butyl ester (23.4 g, 120 mmol) (prepared as described below) in dry THF (275 mL) was added ethylmagnesium chloride (Aldrich, 0.5 M solution in THF, 480 mL, 240 mmol) dropwise at −65° C. and the reaction mixture was stirred at the same temperature for 0.5 hour. The cooling bath was then removed and the reaction mixture was stirred for another 1 hour to give a clear solution. The reaction was quenched by slowly adding EtOH (60 mL) and a saturated aqueous solution of NH$_4$Cl (200 mL) at 5° C., and extracted with ethyl acetate (3×250 mL). The combined organic extracts were successively washed with water (200 mL) and brine (200 mL), dried over anhydrous sodium sulfate, filtered, and concentrated in vacuo. Flash chromatography (Biotage, 75-S, 92/8 hexanes/ethyl acetate) purification of the crude oil afforded 2-(1-hydroxy-prop-2-ynyl)-pyrrole-1-carboxylic acid tert-butyl ester as a light amber oil. (Yield 25.0 g, 94.2%).

The 2-formyl-pyrrole-1-carboxylic acid tert-butyl ester starting material was prepared from 2-formyl-pyrrole according to Tietze, Lutz F.; Kettschau, Georg; Heitmann, Katja.; Synthesis 1996, (7), 851–857.

Example 2

2-tert-Butoxycarbonyloxy-5-fluoro-4-iodo-indole-1-carboxylic acid tert-butyl ester

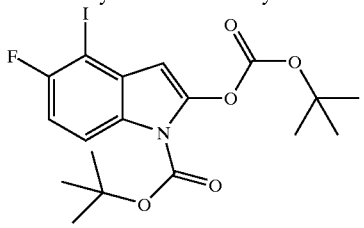

C$_{18}$H$_{21}$FNO$_5$
477.275

To a solution of 5-fluoro-4-iodo-1,3-dihydro-indol-2-one (7.90 g, 28.5 mmol) (prepared as described below) and di-tert-butyl-dicarbonate (Bachem, 18.5 g, 85.5 mmol) in acetonitrile (150 mL) was added DMAP (Aldrich, 0.35 g, 2.9 mmol) in one portion. The reaction mixture was stirred at room temperature for 6 hours, and concentrated in vacuo to remove the solvent (to ~50 mL). The residue was diluted with water (50 mL) and extracted with ethyl acetate (3×150 mL). The combined organic extracts were successively washed with water (100 ml) and brine (100 mL), dried over anhydrous sodium sulfate, filtered, and concentrated in vacuo. Flash chromatography (Biotage, 75-S, 9/1 hexanes/ethyl acetate) afforded 2-tert-butoxycarbonyloxy-5-fluoro-4-iodo-indole-1-carboxylic acid tert-butyl ester as white solid after re-crystallization from hexanes and was used in the next step without further purification. (Yield 7.16 g, 52.0%).

The 5-fluoro-4-iodo-1,3-dihydro-indol-2-one starting material was prepared according to "Preparation of 4-alkynyl-3-(pyrrolylmethylene)-2-oxoindoles as inhibitors of cyclin-dependent kinases, in particular CDK2" Chen, Yi; Corbett, Wendy, L.; Dermatakis, A.; Liu, Jin-Jun; Luk, Kin-Chun; Mahaney, Paige, E.; Mischke, Steven G.; WO 0035908).

Example 3

2-tert-Butoxycarbonyloxy-4-[3-(1-tert-butoxycarbonyl-1H-pyrrol-2-yl)-3-hydroxy-prop-1-ynyl]-5-fluoro-indole-1-carboxylic acid tert-butyl ester

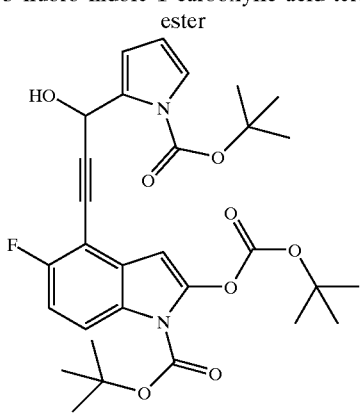

A solution of 2-tert-butoxycarbonyloxy-5-fluoro-4-iodo-indole-1-carboxylic acid tert-butyl ester (from Example 2 above) (9.85 g, 20.0 mmol), and 2-(1-hydroxy-prop-2-ynyl)-pyrrole-1-carboxylic acid tert-butyl ester (from Example 1 above) (7.96 g, 36.0 mmol) in dry THF (85 mL) and triethylamine (Aldrich, 85 mL) was degassed by bubbling argon through the solution for 15 minutes. At this time copper(I) iodide (0.61 g, 3.2 mmol) and (Ph$_3$P)$_4$Pd (Aldrich, 1.85 g, 1.6 mmol) were added, and the reaction mixture was stirred at room temperature for 3.5 hours. The reaction mixture was then poured into a saturated aqueous ammonium chloride solution (100 mL) and extracted with ethyl acetate (3×150 mL). The combined organic extracts were successively washed with water (100 mL) and brine (100 mL), dried over anhydrous sodium sulfate, filtered, and concentrated in vacuo. Flash chromatography (Biotage, 75-S, 9/1 hexanes/ethyl acetate) afforded 2-tert-butoxycarbonyloxy-4-[3-(1-tert-butoxycarbonyl-1H-pyrrol-2-yl)-3-hydroxy-prop-1-ynyl]-5-fluoro-indole-1-carboxylic acid tert-butyl ester as a light orange amorphous solid. (Yield 9.5 g, 83%).

Example 4

2-tert-Butoxycarbonyloxy-4-[3-(1-tert-butoxycarbonyl-1H-pyrrol-2-yl)-3-oxo-prop-1-ynyl]-5-fluoro-4-indole-1-carboxylic acid tert-butyl ester

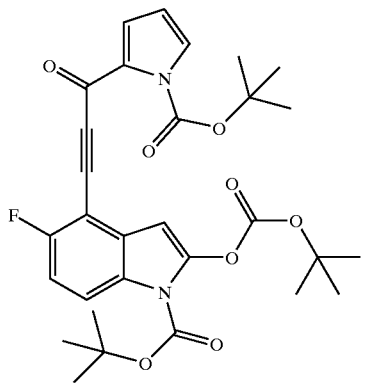

C$_{30}$H$_{33}$FN$_2$O$_8$
568.59

To a solution of 2-tert-butoxycarbonyloxy-4-[3-(1-tert-butoxycarbonyl-1H-pyrrol-2-yl)-3-hydroxy-prop-1-ynyl]-5-fluoro-indole-1-carboxylic acid tert-butyl ester (from Example 3 above) (7.60 g, 13.3 mmol) in CH$_2$Cl$_2$ (400 ml) was added MnO$_2$ (Aldrich, 11.5 g, 130 mmol) in one portion. The reaction mixture was stirred at room temperature overnight and then filtered through Celite® and the solid was washed with CH$_2$Cl$_2$ (200 mL). The combined filtrates was concentrated in vacuo. 2-tert-Butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester was obtained as a light orange amorphous solid which was used in the next step without further purification. (Yield 7.0 g, 92.5%).

Example 5

5-Fluoro-4-[3-oxo-3-(1H-pyrrol-2-yl)-propyl]-1,3-dihydro-indol-2-one

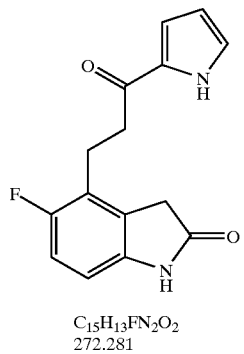

C$_{15}$H$_{13}$FN$_2$O$_2$
272.281

A suspension of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (342.0 mg, 0.60 mmol) and Lindlar catalyst (Aldrich, 250 mg) in dry THF (9 mL) was stirred under hydrogen atmosphere at 45° C. for 3.0 hours. The reaction mixture was then filtered through Celite® and the filtrate was concentrated in vacuo to afford a yellowish amorphous solid. (Yield 331 mg).

The above solid (300 mg) was dissolved in dry CH$_2$Cl$_2$ (2.0 mL) and the solution was treated with TFA (Aldrich, 2.0 mL) at room temperature for 1 hour. The reaction mixture was quenched with a saturated aqueous sodium bicarbonate solution (40 mL) and extracted with ethyl acetate (3×50 mL). The combined organic extracts were successively washed with water (10 mL) and brine (10 mL), dried over anhydrous sodium sulfate, filtered, and concentrated in vacuo to give 5-fluoro-4-[3-oxo-3-(1H-pyrrol-2-yl)-propyl]-1,3-dihydro-indol-2-one as a yellow solid. (Yield 127 mg, 86.7%).

Example 6

6-fluoro-3-(1H-pyrrol-2-yl)-4,5-dihydro-1H-benzo[cd]indol-2-one

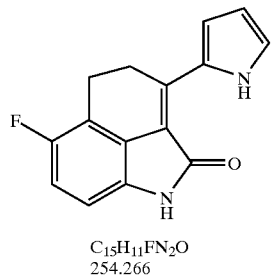

C$_{15}$H$_{11}$FN$_2$O
254.266

A suspension of 5-fluoro-4-[3-oxo-3-(1H-pyrrol-2-yl)-propyl]-1,3-dihydro-indol-2-one (from Example 5 above) (50 mg, 0.184 mmol) in 1.0 N NaOH (10 mL) was heated under reflux overnight. The reaction mixture was diluted with water (20 mL) and extracted with ethyl acetate (3×50 mL). The combined organic extracts were successively washed with water (10 mL) and brine (10 mL), dried over anhydrous sodium sulfate, filtered, and concentrated in vacuo to give 6-fluoro-3-(1H-pyrrol-2-yl)-4,5-dihydro-1H-benzo[cd]indol-2-one as a yellow solid. (Yield 42.2 mg, 90.4%).

Example 7

6-Fluoro-3-(1H-pyrrol-2-yl)-1H-benzo[cd]indol-2-one

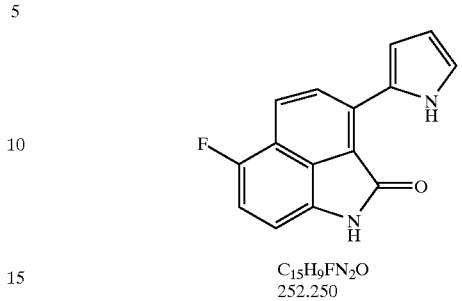

C$_{15}$H$_9$FN$_2$O
252.250

A suspension of 5-fluoro-4-[3-oxo-3-(1H-pyrrol-2-yl)-propyl]-1,3-dihydro-indol-2-one (from Example 5 above) (20 mg, 0.073 mmol) in 1.0 N NaOH (10 mL) was heated under reflux for 2.5 days. The reaction was diluted with water (20 mL) and extracted with ethyl acetate (3×50 mL). The combined organic extracts were successively washed with water (10 mL) and brine (10 mL), dried over anhydrous sodium sulfate, filtered, and concentrated in vacuo to give 6-fluoro-3-(1H-pyrrol-2-yl)-1H-benzo[cd]indol-2-one as a yellow solid. (Yield 16.5 mg, 89.0%).

Example 8

(Z)-5-Fluoro-4-[1-iodo-3-oxo-3-(1H-pyrrol-2-yl)-propenyl]-1,3-dihydro-indol-2-one

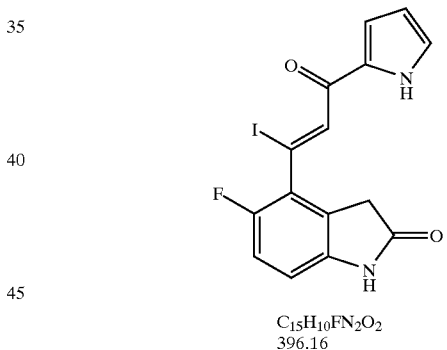

C$_{15}$H$_{10}$FN$_2$O$_2$
396.16

To a mixture of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (5.90 g, 10.4 mmol) and sodium iodide (Aldrich, 4.67 g, 31.4 mmol) was added TFA (Aldrich, 35 mL) slowly at room temperature. The reaction mixture was stirred at room temperature for 30 minutes, and then poured into a mixture of a saturated aqueous sodium bicarbonate solution (400 mL) and ethyl acetate (500 mL). After separation, the aqueous layer was extracted with ethyl acetate (3×100 mL). The combined organic extracts were successively washed with water (200 mL) and brine (200 mL), dried over anhydrous sodium sulfate, filtered, and concentrated in vacuo. The crude product was triturated with ethyl acetate, filtered, and dried to give (Z)-5-fluoro-4-[1-iodo-3-oxo-3-(1H-pyrrol-2-yl)-propenyl]-1,3-dihydro-indol-2-one as a brown solid which was used in the next step without further purification. (Yield 3.86 g, 93.7%).

Example 9

5-(2-Amino-ethylamino)-6-fluoro-3-(1H-pyrrol-2-yl)-1H-benzo[cd]indol-2-one

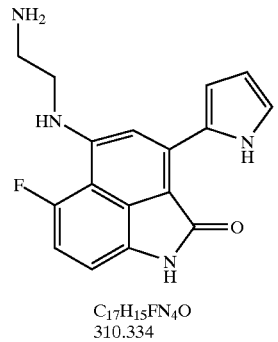

C₁₇H₁₅FN₄O
310.334

To a suspension of (Z)-5-fluoro-4-[1-iodo-3-oxo-3-(1H-pyrrol-2-yl)-propenyl]-1,3-dihydro-indol-2-one (from Example 8 above) (1.58 g, 4.0 mmol) in ethylenediamine (Aldrich, 70 mL) was added NaH (Aldrich, 95%, 1.0 g, 40 mmol) in small portions at room temperature. After stirring at room temperature for 30 minutes, the reaction mixture was heated to 120° C. for 1.5 hours. The reaction was quenched by pouring the reaction mixture into an ice-cold saturated aqueous ammonium chloride solution (200 mL) and extracted with ethyl acetate (3×150 mL). The combined organic extracts were successively washed with water (100 mL) and brine (100 mL), dried over anhydrous sodium sulfate, filtered, and concentrated in vacuo to give crude 5-(2-amino-ethylamino)-6-fluoro-3-(1H-pyrrol-2-yl)-1H-benzo[cd]indol-2-one as a brown solid. (Yield 1.1 g, 88.7%).

Example 10

5-(2-Amino-ethylamino)-6-fluoro-3-(1H-pyrrol-2-yl)-1H-benzo[cd]indol-2-one hydrochloride salt

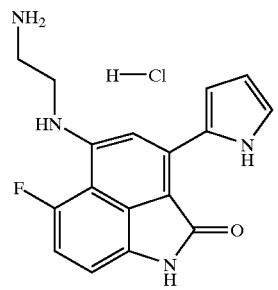

5-(2-Amino-ethylamino)-6-fluoro-3-(1H-pyrrol-2-yl)-1H-benzo[cd]indol-2-one (from Example 9 above) (350 mg, 1.13 mmol) was dissolved in hot 1,4-dioxane (Fisher Scientific, 22 mL) and the solution was filtered through a glass filter. To the clear filtrate was added dropwise 1 N HCl solution in 1,4-dioxane (Aldrich, 3 mL) at room temperature. The precipitate was collected and washed with 1,4-dioxane, ether and dried in vacuo to give 5-(2-amino-ethylamino)-6-fluoro-3-(1H-pyrrol-2-yl)-1H-benzo[cd]indol-2-one hydrochloride salt as a yellow solid. (Yield 212 mg, 54.0%).

Example 11

5-(2-Amino-ethylamino)-6-fluoro-3-(1H-pyrrol-2-yl)-1H-benzo[cd]indol-2-one methanesulfonic acid salt

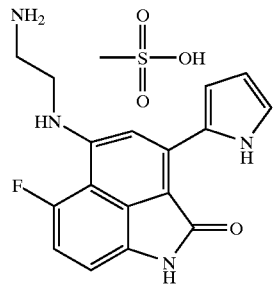

5-(2-Amino-ethylamino)-6-fluoro-3-(1H-pyrrol-2-yl)-1H-benzo[cd]indol-2-one (from Example 9 above) (1.38 g, 4.4 mmol) was dissolved in hot 1,4-dioxane (100 mL) and the solution was filtered through a glass filter. To the clear filtrate was added dropwise a solution of methanesulfonic acid (Aldrich, 380 mg, 3.95 mmol) in 1,4-dioxane (5 mL) at room temperature and the mixture was then allowed to stir for 10 minutes. The precipitate was collected and washed with 1,4-dioxane, ether and dried in vacuo to give the crude product (1.52 g) which was re-crystallized from DMF/1,4-dioxane (14 mL/50 mL) to afford 5-(2-amino-ethylamino)-6-fluoro-3-(1H-pyrrol-2-yl)-1H-benzo[cd]indol-2-one methanesulfonic acid salt as a dark green solid. (Yield 1.0 g, 55.9%).

Example 12

5-(2-Amino-ethylamino)-6-fluoro-3-(1H-pyrrol-2-yl)-1H-benzo[cd]indol-2-one trifluoroacetic acid salt

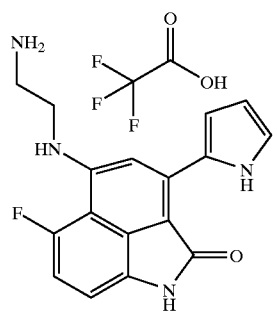

5-(2-Amino-ethylamino)-6-fluoro-3-(1H-pyrrol-2-yl)-1H-benzo[cd]indol-2-one (from Example 9 above) (160 mg, 0.52 mmol) was purified by RP-HPLC (C-18, eluted with 1% acetonitrile/0.05% TFA in H₂O) to afford 5-(2-amino-ethylamino)-6-fluoro-3-(1H-pyrrol-2-yl)-1H-benzo[cd]indol-2-one trifluoroacetic acid salt after lyophilization as a yellow-green solid. (Yield 33 mg, 10.0%).

Example 13

6-Fluoro-5-methoxy-3-(1H-pyrrol-2-yl)-1H-benzo[cd]indol-2-one

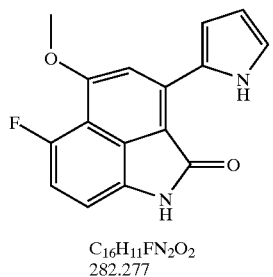

$C_{16}H_{11}FN_2O_2$
282.277

To a suspension of (Z)-5-fluoro-4-[1-iodo-3-oxo-3-(1H-pyrrol-2-yl)-propenyl]-1,3-dihydro-indol-2-one (from Example 8 above) (200 mg, 0.5 mmol) in methanol (20 mL) was added NaH (Aldrich, 60%, 0.6 g, 15 mmol) in portions at room temperature. After stirring at room temperature for 30 minutes, the reaction mixture was heated under reflux for 1.5 hours. The reaction was quenched by pouring the reaction mixture into an ice-cold saturated aqueous ammonium chloride solution (20 mL) and extracted with ethyl acetate (3×50 mL). The combined organic extracts were successively washed with water (10 mL) and brine (10 mL), dried over anhydrous sodium sulfate, filtered, and concentrated in vacuo. The crude product was purified by flash chromatography (silica gel, 25% ethyl acetate in hexanes) to give 6-fluoro-5-methoxy-3-(1H-pyrrol-2-yl)-1H-benzo[cd]indol-2-one as a yellow solid. (Yield 73.2 mg, 51.9%).

Example 14

5-Ethoxy-6-fluoro-3-(1H-pyrrol-2-yl)-1H-benzo[cd]indol-2-one

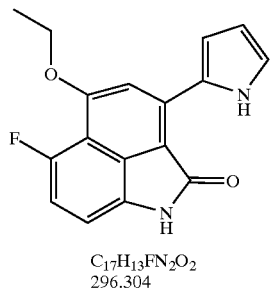

$C_{17}H_{13}FN_2O_2$
296.304

To a suspension of (Z)-5-fluoro-4-[1-iodo-3-oxo-3-(1H-pyrrol-2-yl)-propenyl]-1,3-dihydro-indol-2-one (from Example 8 above) (19.8 mg, 0.05 mmol) in EtOH (5 mL) was added NaH (Aldrich, 60%, 0.1 g, 2.5 mmol) in portions at room temperature. After stirring at room temperature for 30 minutes, the reaction mixture was heated under reflux for 2 hours. The reaction was quenched by pouring the reaction mixture into an ice-cold saturated aqueous ammonium chloride solution (10 mL) and extracted with ethyl acetate (3×20 mL). The combined organic extracts were successively washed with water (10 mL) and brine (10 mL), dried over anhydrous sodium sulfate, filtered, and concentrated in vacuo. The crude product was purified by preparative TLC (silica gel, 50% ethyl acetate in hexanes) to afford 5-ethoxy-6-fluoro-3-(1H-pyrrol-2-yl)-1H-benzo[cd]indol-2-one as a yellow solid. (Yield 3.0 mg, 20.1%).

Example 15

6-Fluoro-5-(2-hydroxy-ethylamino)-3-(1H-pyrrol-2-yl)-1H-benzo[cd]indol-2-one

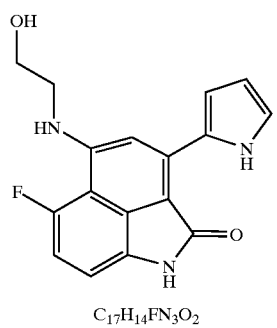

$C_{17}H_{14}FN_3O_2$
311.318

To a solution of (Z)-5-fluoro-4-[1-iodo-3-oxo-3-(1H-pyrrol-2-yl)-propenyl]-1,3-dihydro-indol-2-one (from Example 8 above) (396 mg, 1.0 mmol) in DMF (4.0 mL) and ethanolamine (Aldrich, 0.6 mL, 610 mg, 10.0 mmol) was added NaH (Aldrich, 95%, 270 mg, 10.0 mmol) in portions at 0° C. After stirring at the same temperature for 10 minutes, the reaction mixture was heated to 130° C. for 2 hours. The reaction was quenched by pouring the reaction mixture into an ice-cold saturated aqueous ammonium chloride solution (30 mL) and extracted with ethyl acetate (3×50 mL). The combined organic extracts were successively washed with water (20 mL) and brine (20 mL), dried over anhydrous sodium sulfate, filtered, and concentrated in vacuo. The crude product was purified by flash chromatography (silica gel, 20% ethyl acetate in hexanes) to afford 6-fluoro-5-(2-hydroxy-ethylamino)-3-(1H-pyrrol-2-yl)-1H-benzo[cd]indol-2-one as a yellow solid. (Yield 25.0 mg, 8.0%).

Example 16

6-Fluoro-5-(2-hydroxyethoxy)-3-(1H-pyrrol-2-yl)-1H-benzo[cd]indol-2-one

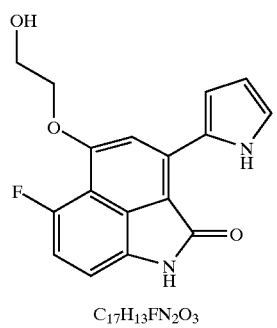

$C_{17}H_{13}FN_2O_3$
312.303

To a suspension of (Z)-5-fluoro-4-[1-iodo-3-oxo-3-(1H-pyrrol-2-yl)-propenyl]-1,3-dihydro-indol-2-one (from Example 8 above) (396 mg, 1.0 mmol) in ethylene glycol (Fisher Scientific, 60 mL) was added NaH (Aldrich, 95%, 2.0 g, 79.2 mmol) in portions at room temperature. After stirring at room temperature for 30 minutes, the reaction mixture was heated under reflux for 2 hours. The reaction was quenched by pouring the reaction mixture into an ice-cold saturated aqueous ammonium chloride solution (100 mL) and extracted with ethyl acetate (3×200 mL). The combined organic extracts were successively washed with water (100 mL) and brine (100 mL), dried over anhydrous sodium sulfate, filtered, and concentrated in vacuo. The crude product was purified by flash chromatography (silica gel, 50% ethyl acetate in hexanes) to give 6-fluoro-5-(2-hydroxy-ethoxy)-3-(1H-pyrrol-2-yl)-1H-benzo[cd]indol-2-one as a yellow solid. (Yield 127.0 mg, 40.7%).

Example 17

6-Fluoro-5-(3-hydroxy-propoxy)-3-(1H-pyrrol-2-yl)-1H-benzo[cd]indol-2-one

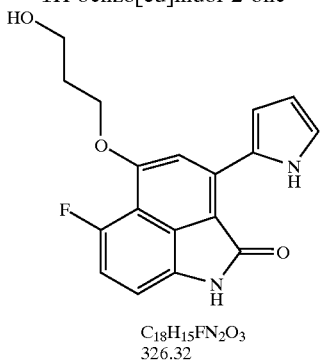

$C_{18}H_{15}FN_2O_3$
326.32

To a suspension of (Z)-5-fluoro-4-[1-iodo-3-oxo-3-(1H-pyrrol-2-yl)-propenyl]-1,3-dihydro-indol-2-one (from Example 8 above) (198 mg, 0.5 mmol) in 1,3-propanediol (Fluka, 7.0 g, 92 mmol) was added NaH (Aldrich, 60%, 0.5 g, 12.5 mmol) in portions at room temperature. After stirring at room temperature for 30 minutes, the reaction mixture was heated to 110° C. for 2.5 hours. The reaction was quenched by pouring the reaction mixture into an ice-cold saturated aqueous ammonium chloride solution (50 mL) and extracted with ethyl acetate (3×50 mL). The combined organic extracts were successively washed with water (20 mL) and brine (20 mL), dried over anhydrous sodium sulfate, filtered, and concentrated in vacuo. The crude product was purified by flash chromatography (silica gel, 50% ethyl acetate in hexanes) to afford 6-fluoro-5-(3-hydroxy-propoxy)-3-(1H-pyrrol-2-yl)-1H-benzo[cd]indol-2-one as a yellow solid. (Yield 51.5 mg, 31.6%).

Example 18

[2-[6-Fluoro-2-oxo-3-(1H-pyrrol-2-yl)-1,2-di hydro-benzo[cd]indol-5-yloxy]-ethyl]-carbamic acid tert-butyl ester

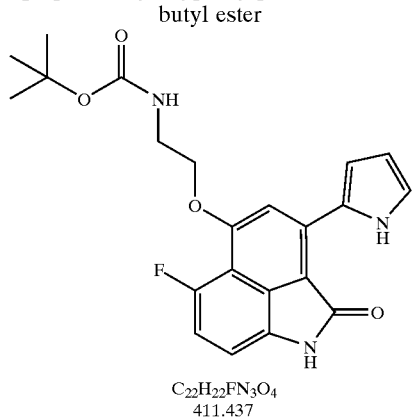

$C_{22}H_{22}FN_3O_4$
411.437

To a suspension of (Z)-5-fluoro-4-[1-iodo-3-oxo-3-(1H-pyrrol-2-yl)-propenyl]-1,3-dihydro-indol-2-one (from Example 8 above) (79.2 mg, 0.2 mmol) in tert-butyl N-(2-hydroxyethyl)-carbamate (Aldrich, 3 mL, 18.9 mmol) was added NaH (Aldrich, 60%, 0.2 g, 5.0 mmol) in portions at room temperature. After stirring at room temperature for 30 minutes, the reaction mixture was heated to 120° C. for 3.0 hours. The reaction was quenched by pouring the reaction mixture into an ice-cold saturated aqueous ammonium chloride solution (20 mL) and extracted with ethyl acetate (3×30 mL). The combined organic extracts were successively washed with water (10 mL) and brine (10 mL), dried over anhydrous sodium sulfate, filtered, and concentrated in vacuo. The crude product was purified by flash chromatography (silica gel, 50% ethyl acetate in hexanes) to give [2-[6-fluoro-2-oxo-3-(1H-pyrrol-2-yl)-1,2-dihydro-benzo[cd]indol-5-yloxy]-ethyl]-carbamic acid tert-butyl ester as a yellow solid. (Yield 17.7 mg, 21.5%).

Example 19

5-(2-Amino-ethoxy)-6-fluoro-3-(1H-pyrrol-2-yl)-1H-benzo[cd]indol-2-one

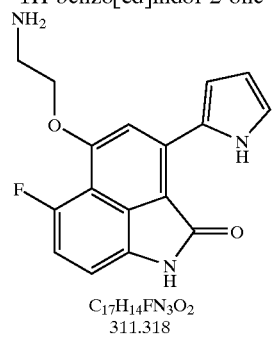

$C_{17}H_{14}FN_3O_2$
311.318

To a solution of [2-[6-fluoro-2-oxo-3-(1H-pyrrol-2-yl)-1,2-dihydro-benzo[cd]indol-5-yloxy]-ethyl]-carbamic acid tert-butyl ester (from Example 18 above) (16.5 mg, 0.2 mmol) in $CH_2Cl_2$ (1 mL) was added trifluoroacetic acid (0.5 mL) at room temperature. After stirring at room temperature for 30 minutes, the reaction mixture was quenched with 1.0 N NaOH (2.0 mL) and extracted with ethyl acetate (3×30 mL). The combined organic extracts were successively washed with water (10 mL) and brine (10 mL), dried over anhydrous sodium sulfate, filtered, and concentrated in vacuo to give 5-(2-amino-ethoxy)-6-fluoro-3-(1H-pyrrol-2-yl)-1H-benzo[cd]indol-2-one as a yellow solid. (Yield 11.2 mg, 89.7%).

Example 20

5-(2-Amino-ethoxy)-6-fluoro-3-(1H-pyrrol-2-yl)-1H-benzo[cd]indol-2-one methanesulfonic acid salt

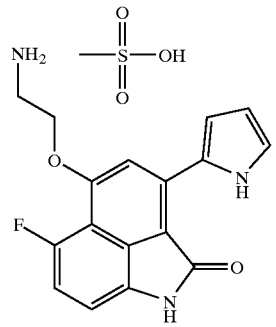

5-(2-Amino-ethoxy)-6-fluoro-3-(1H-pyrrol-2-yl)-1H-benzo[cd]indol-2-one (from Example 19 above) (62.3 mg, 0.20 mmol) was dissolved in hot 1,4-dioxane (2.5 mL) and the solution was filtered through a glass filter. To the clear filtrate was added dropwise a solution of methanesulfonic acid (Aldrich, 16.0 mg, 0.16 mmol) in 1,4-dioxane (0.2 mL) at room temperature and the mixture was stirred for 10 minutes. The precipitate formed was collected and washed with 1,4-dioxane, ether and dried in vacuo to afford 5-(2-amino-ethoxy)-6-fluoro-3-(1H-pyrrol-2-yl)-1H-benzo[cd]indol-2-one methanesulfonic acid salt as a yellow solid. (Yield 52.5 mg, 64.5%).

Example 21

5-(3-Amino-propylamino)-6-fluoro-3-(1H-pyrrol-2-yl)-1H-benzo[cd]indol-2-one acetic acid salt

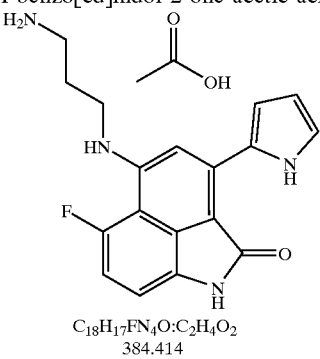

$C_{18}H_{17}FN_4O:C_2H_4O_2$
384.414

To a suspension of (Z)-5-fluoro-4-[1-iodo-3-oxo-3-(1H-pyrrol-2-yl)-propenyl]-1,3-dihydro-indol-2-one (from Example 8 above) (118.8 mg, 0.3 mmol) in 1,3-diaminopropane (Aldrich, 3 mL, 35.6 mmol) was added NaH (Aldrich, 90%, 53 mg, 6.6 mmol) in portions at room temperature. After stirring at room temperature for 30 minutes, the reaction mixture was heated to 120° C. for 2.5 hours. The reaction was quenched by pouring the reaction mixture into an ice-cold saturated aqueous ammonium chloride solution (20 mL) and extracted with ethyl acetate (3×30 mL). The combined organic extracts were successively washed with water (10 mL) and brine (10 mL), dried over anhydrous sodium sulfate, filtered, and concentrated in vacuo to give 5-(3-amino-propylamino)-6-fluoro-3-(1H-pyrrol-2-yl)-1H-benzo[cd]indol-2-one (Yield 25.3 mg, 26.0%) as the free base which was further purified by RP-HPLC (C-18, eluted with 1% acetonitrile/0.05% acetic acid in $H_2O$) to afford 5-(3-amino-propylamino)-6-fluoro-3-(1H-pyrrol-2-yl)-1H-benzo[cd]indol-2-one acetic acid salt.

Example 22

5-(2-Amino-2-methyl-propylamino)-6-fluoro-3-(1H-pyrrol-2-yl)-1H-benzo[cd]indol-2-one

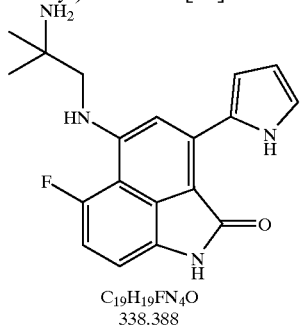

$C_{19}H_{19}FN_4O$
338.388

To a suspension of (Z)-5-fluoro-4-[1-iodo-3-oxo-3-(1H-pyrrol-2-yl)-propenyl]-1,3-dihydro-indol-2-one (from Example 8 above) (79.2 mg, 0.2 mmol) in 1,2-diamino-2-methylpropane (Aldrich, 3 mL, 28.4 mmol) was added NaH (Aldrich, 90%, 36 mg, 1.4 mmol) in portions at room temperature. After stirring at room temperature for 30 minutes, the reaction mixture was heated under reflux for 1 hour. The reaction was quenched by pouring the reaction mixture into an ice-cold saturated aqueous ammonium chloride solution (10 mL) and extracted with ethyl acetate (3×20 mL). The combined organic extracts were successively washed with water (10 mL) and brine (10 mL), dried over anhydrous sodium sulfate, filtered, and concentrated in vacuo. The crude product was purified by preparative TLC (silica gel, 5% methanol in ethyl acetate) to afford 5-(2-amino-2-methyl-propylamino)-6-fluoro-3-(1H-pyrrol-2-yl)-1H-benzo[cd]indol-2-one as a brown solid. (Yield 4.4 mg, 6.5%).

Example 23

6-Fluoro-5-morpholin-4-yl-3-(1H-pyrrol-2-yl)-1H-benzo[cd]indol-2-one

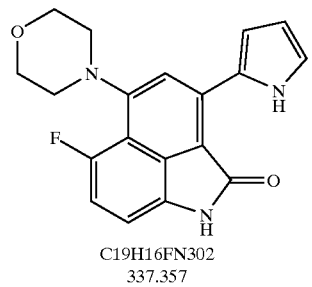

$C_{19}H_{16}FN_3O_2$
337.357

To a flask charged with 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (220 mg, 0.39 mmol) was added morpholine (Aldrich, 2 mL, 23 mmol) and the red solution was stirred under argon at room temperature for 10 minutes. The reaction was then quenched by pouring the reaction mixture into an ice-cold saturated aqueous ammonium chloride solution (50 mL) and extracted with ethyl acetate (3×50 mL). The combined organic extracts were successively washed with water (50 mL) and brine (50 mL), dried over anhydrous sodium sulfate, filtered, and concentrated in vacuo. The residue obtained was re-dissolved in $CH_2Cl_2$ (2 mL) and treated with trifluoroacetic acid at 0° C. for 1 hour. The reaction was then quenched with a saturated aqueous sodium bicarbonate solution (5 mL) and extracted with ethyl acetate (3×10 mL). The combined organic extracts were successively washed with water (5 mL) and brine (5 mL), dried over anhydrous sodium sulfate, filtered, and concentrated in vacuo. The dark-brown material was then suspended in 0.5 N NaOH (8 mL) and heated to 90° C. for 6 hours. The reaction was quenched by pouring the reaction mixture into an ice-cold saturated aqueous ammonium chloride solution (10 mL) and extracted with ethyl acetate (3×20 mL). The combined organic extracts were successively washed with water (10 mL) and brine (10 mL), dried over anhydrous sodium sulfate, filtered, and concentrated in vacuo. The crude product was purified by preparative TLC (silica gel, 50% ethyl acetate in hexanes) to afford 6-fluoro-5-morpholin-4-yl-3-(1H-pyrrol-2-yl)-1H-benzo[cd]indol-2-one as a yellow solid. (Yield 15.1 mg, 11.6%).

Example 24

6-Fluoro-5-piperazin-1-yl-3-(1H-pyrrol-2-yl)-1H-benzo[cd]indol-2-one acetic acid salt

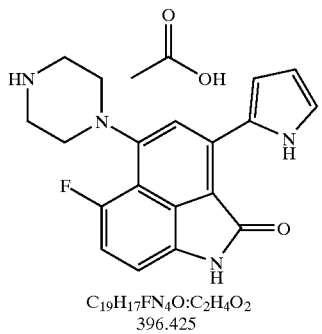

$C_{19}H_{17}FN_4O:C_2H_4O_2$
396.425

To a suspension of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (310 mg, 0.54 mmol) in $CH_2Cl_2$ (2 mL) was added piperazine (Aldrich, 56 mg, 65 mmol) and the red solution was stirred under argon at room temperature for 30 minutes. The reaction was then quenched by pouring the reaction mixture into an ice-cold saturated aqueous ammonium chloride solution (50 mL) and extracted with ethyl acetate (3×50 mL). The combined organic extracts were successively washed with water (50 mL) and brine (50 mL), dried over anhydrous sodium sulfate, filtered, and concentrated in vacuo.

The brown solid obtained was re-dissolved in $CH_2Cl_2$ (5 mL) and treated with piperazine (Aldrich, 340 mg, 395 mmol) at room temperature for 5 hours. The reaction was then quenched by pouring the reaction mixture into an ice-cold saturated aqueous ammonium chloride solution (50 mL) and extracted with ethyl acetate (3×50 mL). The combined organic extracts were successively washed with water (50 mL) and brine (50 mL), dried over anhydrous sodium sulfate, filtered, and concentrated in vacuo.

The dark-brown residue was then suspended in 0.5 N NaOH (5 mL) and heated under reflux overnight. The reaction was diluted with water (10 mL) and extracted with ethyl acetate (3×20 mL). The combined organic extracts were successively washed with water (10 mL) and brine (10 mL), dried over anhydrous sodium sulfate, filtered, and concentrated in vacuo. The crude product was purified by RP-HPLC (C-18, eluted with 1% acetonitrile/0.05% acetic acid in $H_2O$) to afford 6-fluoro-5-piperazin-1-yl-3-(1H-pyrrol-2-yl)-1H-benzo[cd]indol-2-one acetic acid salt as a yellow solid. (Yield 9.5 mg, 4.4%).

Example 25

6-Fluoro-5-methyl-3-(1H-pyrrol-2-yl)-1H-benzo[cd]indol-2-one

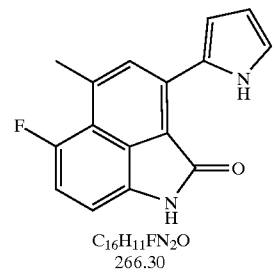

$C_{16}H_{11}FN_2O$
266.30

To a suspension of copper(I) iodide (Aldrich, 190 mg, 1.0 mmol) in dry THF (2 mL) was added methyllithium (Aldrich, 1.4 M solution in ether, 1.42 mL, 2.0 mmol), under argon, at 0° C. and the reaction mixture was stirred for 15 minutes. To the colorless solution obtained was added dropwise a solution of (Z)-5-fluoro-4-[1-iodo-3-oxo-3-(1H-pyrrol-2-yl)-propenyl]-1,3-dihydro-indol-2-one (from Example 8 above) (39.6 mg, 0.1 mmol) in THF (2 mL). After stirring at 0° C. for another 45 minutes, the reaction mixture was quenched with a saturated aqueous ammonium chloride solution (10 mL) and extracted with ethyl acetate (3×20 mL). The combined organic extracts were successively washed with water (10 mL) and brine (10 mL), dried over anhydrous sodium sulfate, filtered, and concentrated in vacuo to give crude product (28.5 mg) which was further purified by preparative TLC (silica gel, 20% ethyl acetate in hexanes) to afford 6-fluoro-5-methyl-3-(1H-pyrrol-2-yl)-1H-benzo[cd]indol-2-one as a yellow solid. (Yield 12.6 mg, 47.4%).

Example 26

(rac)-5-sec-Butyl-6-fluoro-3-(1H-pyrrol-2-yl)-1H-benzo[cd]indol-2-one

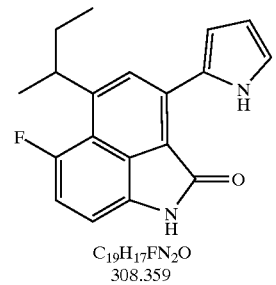

$C_{19}H_{17}FN_2O$
308.359

To a suspension of copper(I) iodide (Aldrich, 190 mg, 1.0 mmol) in dry THF (2 mL) was added sec-butyllithium (Aldrich, 1.3 M solution in ether, 1.53 mL, 2.0 mmol), under argon, at 0° C. and the reaction mixture was stirred for 30 minutes. To the resulting brown solution obtained was added dropwise a solution of (Z)-5-fluoro-4-[1-iodo-3-oxo-3-(1H-pyrrol-2-yl)-propenyl]-1,3-dihydro-indol-2-one (from Example 8 above) (39.6 mg, 0.1 mmol) in THF (2 mL). After stirring at 0° C. for 45 minutes, the reaction mixture was stirred at room temperature for another 2 hours, then quenched with a saturated aqueous ammonium chloride solution (10 mL) and extracted with ethyl acetate (3×20 mL). The combined organic extracts were successively washed with water (10 mL) and brine (10 mL), dried over anhydrous sodium sulfate, filtered, and concentrated in vacuo to give crude product which was further purified by preparative TLC (silica gel, 20% ethyl acetate in hexanes) to afford (rac)-5-sec-butyl-6-fluoro-3-(1H-pyrrol-2-yl)-1H-benzo[cd]indol-2-one as a yellow solid. (Yield 3.6 mg, 11.7%).

Example 27

5-Ethyl-6-fluoro-3-(1H-pyrrol-2-yl)-1H-benzo[cd]indol-2-one

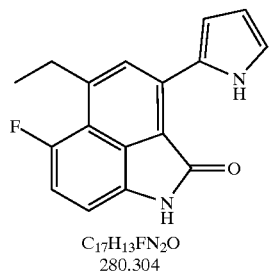

$C_{17}H_{13}FN_2O$
280.304

To a suspension of copper(I) cyanide (Aldrich, 27 mg, 0.3 mmol) and lithium chloride (Fluka, 25.5 mg, 0.6 mmol) in dry THF (2 mL) was added diethylzinc (Aldrich, 1.0 M solution in n-hexane, 3.0 mL, 3.0 mmol), under argon, at −20° C. and the reaction mixture was stirred for 30 minutes at the same temperature. The light green reaction mixture was then cooled to −78° C. and treated dropwise with a solution of (Z)-5-fluoro-4-[1-iodo-3-oxo-3-(1H-pyrrol-2-yl)-propenyl]-1,3-dihydro-indol-2-one (from Example 8 above) (79.2 mg, 0.2 mmol) in dry THF (4 mL). After stirring at the same temperature for 1 hour, the reaction mixture was allowed to warm up slowly to room temperature overnight, then heated under reflux for 3 hours. The reaction mixture was quenched with a saturated aqueous ammonium chloride solution (20 mL) and extracted with ethyl acetate (3×30 mL). The combined organic extracts were successively washed with water (20 mL) and brine (20 mL), dried over anhydrous sodium sulfate, filtered, and concentrated in vacuo to give crude product which was further purified by preparative TLC (silica gel, 20% ethyl acetate in hexanes) to afford 5-ethyl-6-fluoro-3-(1H-pyrrol-2-yl)-1H-benzo[cd]indol-2-one as a yellow solid. (Yield 10.6 mg, 18.9%).

Example 28

6-Fluoro-5-(2-oxo-imidazolidin-1-yl)-3-(1H-pyrrol-2-yl)-1H-benzo[cd]indol-2-one

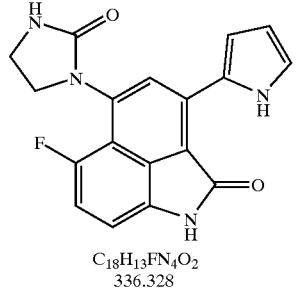

$C_{18}H_{13}FN_4O_2$
336.328

To a suspension of 5-(2-amino-ethylamino)-6-fluoro-3-(1H-pyrrol-2-yl)-1H-benzo[cd]indol-2-one (from Example 9 above) (31.1 mg, 0.1 mmol) in 1,2-dichloroethane (3 mL) was added 1,1′-carbonyldiimidazole (Aldrich, 162 mg, 1.0 mmol) at room temperature. The reaction mixture was heated under reflux overnight. The reaction was then quenched with saturated aqueous sodium bicarbonate solution (5 mL) and extracted with ethyl acetate (3×10 mL). The combined organic extracts were successively washed with water (5 mL) and brine (5 mL), dried over anhydrous sodium sulfate, filtered, and concentrated in vacuo. The crude product was triturated with ethyl acetate and hexanes, filtered, and dried to give 6-fluoro-5-(2-oxo-imidazolidin-1-yl)-3-(1H-pyrrol-2-yl)-1H-benzo[cd]indol-2-one as a yellow solid. (Yield 19.5 mg, 58.0%).

Example 29

N-[2-[6-Fluoro-2oxo-3-(1H-pyrrol-2-yl)-1,2-dihydro-benzo[cd]indol-5-ylamino]-ethyl]-acetamide

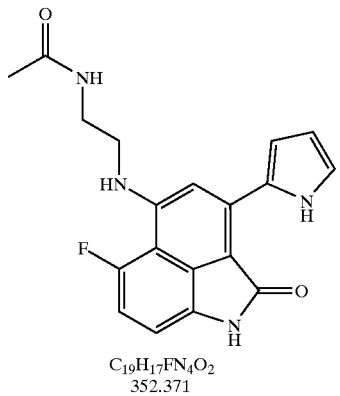

$C_{19}H_{17}FN_4O_2$
352.371

To a suspension of 5-(2-amino-ethylamino)-6-fluoro-3-(1H-pyrrol-2-yl)-1H-benzo[cd]indol-2-one hydrochloride salt (from Example 10 above) (35.5 mg, 0.1 mmol) in $CH_2Cl_2$ (2 mL) were added acetic anhydride (Fisher Scientific, 10.2 mg, 0.1 mmol) and triethylamine (Aldrich, 20.2 mg, 0.2 mmol) at room temperature. The reaction mixture was stirred for 2 hours at the same temperature and then quenched with a saturated aqueous ammonium chloride solution (5 mL) and extracted with ethyl acetate (3×10 mL). The combined organic extracts were successively washed with water (5 mL) and brine (5 mL), dried over anhydrous sodium sulfate, filtered, and concentrated in vacuo. The crude product was triturated with ethyl acetate and hexanes, filtered, and dried to give N-[2-[6-fluoro-2-oxo-3-(1H-pyrrol-2-yl)-1,2-dihydro-benzo[cd]indol-5-ylamino]-ethyl]-acetamide as a brown solid. (Yield 13.5 mg, 38.4%).

Example 30

5-(2-Dimethylamino-ethylamino)-6-fluoro-3-(1H-pyrrol-2-yl)-1H-benzo[cd]indol-2-one trifluoroacetic acid salt

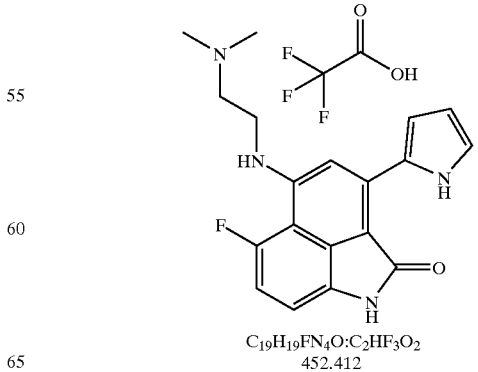

$C_{19}H_{19}FN_4O:C_2HF_3O_2$
452.412

33

To a suspension of 5-(2-amino-ethylamino)-6-fluoro-3-(1H-pyrrol-2-yl)-1H-benzo[cd]indol-2-one hydrochloride salt (from Example 10 above) (69.4 mg, 0.2 mmol) in CH$_2$Cl$_2$ (5 mL) were added paraformaldehyde (Aldrich, 10.0 mg, 0.32 mmol) and sodium cyanoborohydride (Aldrich, 20.0 mg, 0.32 mmol) at room temperature. The reaction mixture was stirred overnight. The reaction was then quenched with water (5 mL) and extracted with ethyl acetate (3×20 mL). The combined organic extracts were successively washed with water (5 mL) and brine (5 mL), dried over anhydrous sodium sulfate, filtered, and concentrated in vacuo. The crude product was purified by RP-HPLC (C-18, eluted with 1% acetonitrile/0.05% TFA in H$_2$O) to give 5-(2-dimethylamino-ethylamino)-6-fluoro-3-(1H-pyrrol-2-yl)-1H-benzo[cd]indol-2-one trifluoroacetic acid salt as a brown solid. (Yield 10.0 mg, 11.1%).

Example 31

5-(2-Diethylamino-ethylamino)-6-fluoro-3-(1H-pyrrol-2-yl)-1H-benzo[cd]indol-2-one

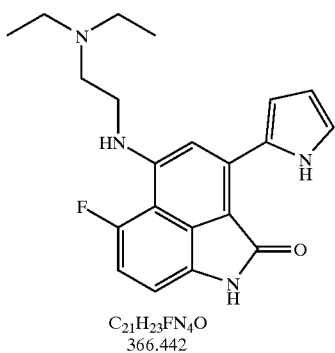

C$_{21}$H$_{23}$FN$_4$O
366.442

To a suspension of 5-(2-amino-ethylamino)-6-fluoro-3-(1H-pyrrol-2-yl)-1H-benzo[cd]indol-2-one methanesulfonic acid salt (from Example 11 above) (58.04 mg, 0.14 mmol) in CH$_2$Cl$_2$ (5 mL) were added acetaldehyde (Aldrich, 0.39 mg, 0.39 mmol) and sodium cyanoborohydride (Aldrich, 20.0 mg, 0.32 mmol) at room temperature. The reaction mixture was stirred for 1 hour. The reaction was then quenched with water (5 mL) and extracted with ethyl acetate (3×20 mL). The combined organic extracts were successively washed with water (5 mL) and brine (5 mL), dried over anhydrous sodium sulfate, filtered, and concentrated in vacuo. The crude product was triturated with ethyl acetate and hexanes, filtered, and dried to give 5-(2-diethylamino-ethylamino)-6-fluoro-3-(1H-pyrrol-2-yl)-1H-benzo[cd]indol-2-one as a brown solid. (Yield 12.0 mg, 23.4%).

Example 32

6-Fluoro-5-[(R)-3-hydroxy-pyrrolidin-1-yl)]-3-(1H-pyrrol-2-yl)-1H-benzo[cd]indol-2-one

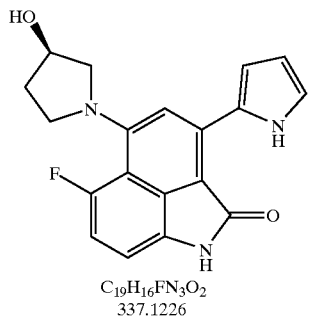

C$_{19}$H$_{16}$FN$_3$O$_2$
337.1226

34

A mixture of (Z)-5-fluoro-4-[1-iodo-3-oxo-3-(1H-pyrrol-2-yl)-propenyl]-1,3-dihydro-indol-2-one (from Example 8 above) (250 mg, 0.504 mmol) and 3-R-hydroxy pyrrolidine (Aldrich, 870 mg, 9.99 mmol) in DMF (5 mL) was treated with NaH (Aldrich, 120 mg, 5.04 mmol). The mixture was stirred at approximately 110° C. for 2.5 hours and then at room temperature overnight. The reaction mixture was poured in a mixture of ethyl acetate and water. The aqueous layer was extracted a few more times with ethyl acetate and the combined organic layer was dried over Na$_2$SO$_4$, filtered, and concentrated. The residue was purified by flash chromatography (silica gel, with 0–100% ethyl acetate in hexanes and then 0–100% THF in ethyl acetate) to give 6-fluoro-5-[(R)-3-hydroxy-pyrrolidin-1-yl)]-3-(1H-pyrrol-2-yl)-1H-benzo[cd]indol-2-one as a yellow-green solid. (Yield 6 mg, 5%).

Example 33

6-Fluoro-5-(4-hydroxy-piperidin-1-yl)-3-(1H-pyrrol-2-yl)-1H-benzo[cd]indol-2-one

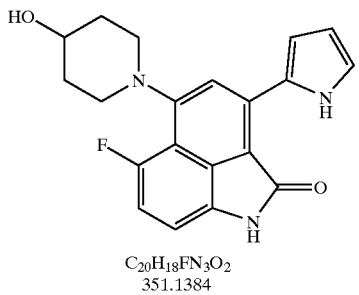

C$_{20}$H$_{18}$FN$_3$O$_2$
351.1384

A mixture of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (392 mg, 0.69 mmol) and 4-hydroxy-piperidine (Aldrich, 2.12 g, 20.94 mmol) in DMF(6 mL) was treated with NaH. (Aldrich, 250 mg, 10.42 mmol). The mixture was stirred for 30 minutes at room temperature and overnight at 120° C. The reaction mixture was poured in a mixture of ethyl acetate and water. The aqueous layer was Example 32

6-Fluoro-5-[(R)-3-hydroxy-pyrrolidin-1-yl)]-3-(1H-pyrrol-2-yl)-1H-benzo[cd]indol-2-one

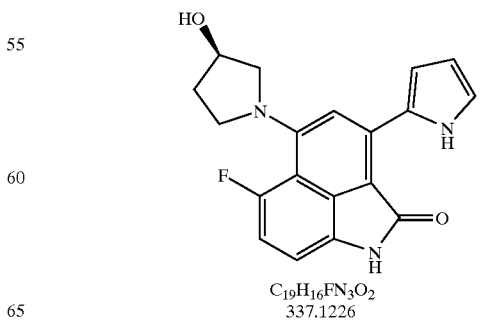

C$_{19}$H$_{16}$FN$_3$O$_2$
337.1226 extracted a few more times with ethyl acetate and the combined organic layer was dried over Na$_2$SO$_4$, filtered, and concentrated. The residue was purified by flash chromatography (silica gel, with 0–50% ethyl acetate in hexanes gradient), and further purified by HPLC (silica gel, 50% ethyl acetate in hexanes) and precipitation out of THF with excess of pentane to give 6-fluoro-5-(4-hydroxy-piperidin-1-yl)-3-(1H-pyrrol-2-yl)-1H-benzo[cd]indol-2-one as a yellow solid. (Yield 85 mg, 38%).

Example 34

6-Fluoro-5-(3-hydroxymethyl-piperidin-1-yl)-3-(1H-pyrrol-2-yl)-1H-benzo[cd]indol-2one

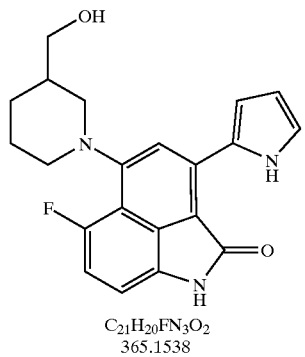

C$_{21}$H$_{20}$FN$_3$O$_2$
365.1538

A mixture of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (230 mg, 0.40 mmol) and 3-hydroxymethyl-piperidine (Aldrich, 1.20 g, 12.10 mmol) in DMF (6 ml) was treated with NaH (Aldrich, 146 mg, 6.08 mmol). After stirring for 30 minutes at room temperature and then 30 hours at 120° C. the mixture was cooled and poured in a mixture of ethyl acetate and water. The aqueous layer was extracted a few more times with ethyl acetate and the combined organic layer was dried over Na$_2$SO$_4$, filtered, and concentrated. The resulting residue was purified by flash chromatography (silica gel,0–50% ethyl acetate in hexanes gradient) and then further purified by HPLC (silica gel, 30% ethyl acetate in hexanes) and precipitation out of THF with excess of pentane to give 6-fluoro-5-(3-hydroxymethyl-piperidin-1-yl)-3-(1H-pyrrol-2-yl)-1H-benzo[cd]indol-2-one as a yellow solid. (Yield 12 mg, 8%).

Example 35

6-Fluoro-5-(3-hydroxy-piperidin-1-yl)-3-(1H-pyrrol-2-yl)-1H-benzo[cd]indol-2-one

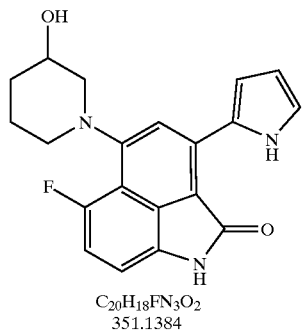

C$_{20}$H$_{18}$FN$_3$O$_2$
351.1384

A mixture of 2-tert-butoxycarbonyloxy-4-[3-(1-tert-butoxycarbonyl-1H-pyrrol-2-yl)-3-oxo-prop-1-ynyl]-5-fluoro-indole-1-carboxylic acid tert-butyl ester (from Example 4 above) (230 mg, 0.40 mmol) and 3-hydroxy-piperidine (Aldrich, 1.23 g, 12.13 mmol) in DMF (15 ml) was heated to 120° C. for 1.5 hours. The mixture was cooled and NaH (Aldrich, 140 mg, 5.83 mmol) was added in small portions with stirring. After 30 minutes at room temperature and then 20 hours at 120° C. the mixture was cooled and poured into a mixture of ethyl acetate and water. The aqueous layer was extracted few more times with ethyl acetate and the combined organic layer was dried over Na$_2$SO$_4$, filtered, and concentrated. The residue was purified by flash chromatography (silica gel, 60% ethyl acetate in hexanes) and further purified by HPLC (silica gel, 35% ethyl acetate in hexanes) and a precipitation out of THF with excess of pentane to give 6-fluoro-5-(3-hydroxy-piperidin-1-yl)-3-(1H-pyrrol-2-yl)-1H-benzo[cd]indol-2-one as a yellow solid. (Yield 45 mg, 31%).

Example 36

6-Fluoro-5-(2-hydroxyethylsulfanyl)-3-(1H-pyrrol-2-yl)-1H-benzo[cd]indol-2-one

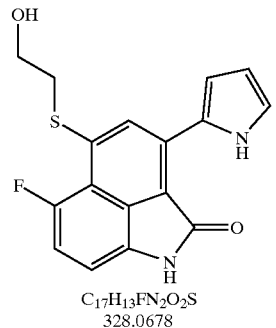

C$_{17}$H$_{13}$FN$_2$O$_2$S
328.0678

A mixture of (Z)-5-fluoro-4-[1-iodo-3-oxo-3-(1H-pyrrol-2-yl)-propenyl]-1,3-dihydro-indol-2-one (from Example 8 above) (300 mg, 0.60 mmol) and neat 2-mercaptoethanol (Sigma, 4 mL) was treated with NaH (Aldrich, 98%, 210 mg that was emulsified with 0.4 mL of mineral oil) in small portions at room temperature. After the evolution of gas stopped, the mixture was heated gradually to 120° C. and stirred at this temperature for 6 hours. The reaction mixture was then poured in a mixture of ethyl acetate and water. The aqueous layer was extracted few more times with ethyl acetate and the combined organic layer was dried over Na$_2$SO$_4$, filtered, and concentrated. The residue was purified by HPLC (silica gel, with 25% ethyl acetate in hexanes) and then precipitated out of THF with excess pentane to give 6-fluoro-5-(2-hydroxy-ethylsulfanyl)-3-(1H-pyrrol-2-yl)-1H-benzo[cd]indol-2-one as a yellow solid. (Yield 98 mg, 49%).

Example 37

6-Fluoro-5-(2-hydroxy-ethanesulfinyl)-3-(1H-pyrrol-2-yl)-1H-benzo[cd]indol-2-one

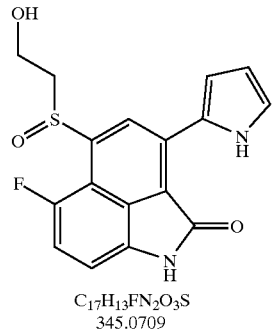

C$_{17}$H$_{13}$FN$_2$O$_3$S
345.0709

A solution of 6-fluoro-5-(2-hydroxy-ethylsulfanyl)-3-(1H-pyrrol-2-yl)-1H-benzo[cd]indol-2-one (from Example 36 above) (15 mg, 0.05 mmol) in THF (approximately 7 mL) was treated with mCPBA (Acros, 14 mg, 0.06 mmol, 75%). After 20 minutes, the reaction mixture was diluted with ethyl acetate and washed with aqueous saturated $Na_2S_2O_3$ and aqueous saturated $NaHCO_3$. The organic layer was dried over $Na_2SO_4$ and concentrated. The resulting residue was purified by flash chromatography (silica gel, 0–100% ethyl acetate in hexanes gradient), followed by precipitation out of THF with excess pentane to give 6-fluoro-5-(2-hydroxy-ethanesulfinyl)-3-(1H-pyrrol-2-yl)-1H-benzo[cd]indol-2-one as a yellow solid. (Yield 15 mg, 96%).

Example 38

6-Fluoro-5-(2-hydroxy-ethanesulfonyl)-3-(1H-pyrrol-2-yl)-1H-benzo[cd]indol-2-one

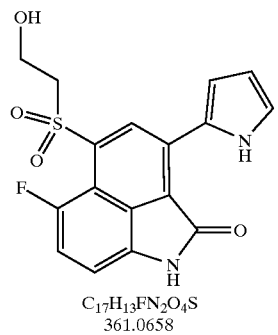

$C_{17}H_{13}FN_2O_4S$
361.0658

A solution of 6-fluoro-5-(2-hydroxy-ethylsulfanyl)-3-(1H-pyrrol-2-yl)-1H-benzo[cd]indol-2-one (from Example 36 above) (40 mg, 0.12 mmol) in THF (approximately 10 mL) was treated with mCPBA (Acros, 50 mg, 0.31 mmol, 75%) at room temperature for 15 minutes and then at 50° C. for 15 hours. The reaction mixture was cooled and then another portion of mCPBA (Acros, 50 mg, 0.31 mmol, 75%) was added. After 6 more hours at 50° C. the reaction mixture was cooled and poured into ethyl acetate. The mixture was washed with aqueous saturated $Na_2S_2O_3$ and aqueous saturated $NaHCO_3$. The organic layer was dried over $Na_2SO_4$ and concentrated. The residue was purified by HPLC (silica gel, 60% ethyl acetate in hexanes), followed by precipitation out of THF with excess pentane to give 6-fluoro-5-(2-hydroxy-ethanesulfonyl)-3-(1H-pyrrol-2-yl)-1H-benzo[cd]indol-2-one as an orange solid. (Yield 23 mg, 52%).

Example 39

[2-[6-Fluoro-2-oxo-3-(1H-pyrrol-2-yl)-1,2-dihydro-benzo[cd]indol-5-ylsulfanyl]-ethyl]-carbamic acid tert-butyl ester

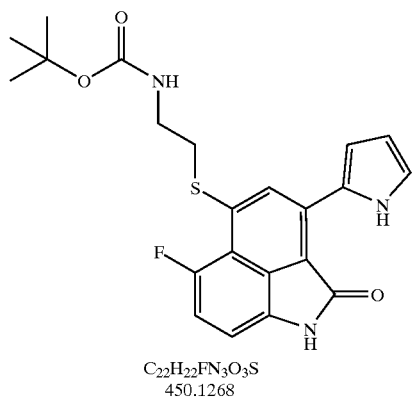

$C_{22}H_{22}FN_3O_3S$
450.1268

A mixture of (Z)-5-fluoro-4-[1-iodo-3-oxo-3-(1H-pyrrol-2-yl)-propenyl]-1,3-dihydro-indol-2-one (from Example 8 above) (600 mg, 1.28 mmol) and neat tert-butyl-N-(2-mercaptoethyl)-carbamate (Aldrich, 19 mL) was treated with NaH (Aldrich, 460 mg, 19.15 mmol) in small portions e within a period of 30 minutes at room temperature. After the evolution of hydrogen had stopped, the mixture was heated gradually to 120° C. The viscous slurry was stirred at this temperature for 2 hours and then allowed to cool. The mixture was partitioned between ethyl acetate and water. The aqueous layer was extracted twice more with ethyl acetate. The combined organic layer was dried and concentrated to give a solid residue. This residue was washed with pentane and purified by HPLC (silica gel, 25% ethyl acetate in hexanes), followed by precipitation out of THF with excess pentane to give [2-[6-fluoro-2-oxo-3-(1H-pyrrol-2-yl)-1,2-dihydro-benzo[cd]indol-5-ylsulfanyl]-ethyl]-carbamic acid tert-butyl ester as a yellow solid. (Yield 470 mg, 84%).

Example 40

5-(2-Amino-ethylsulfanyl)-6-fluoro-3-(1H-pyrrol-2-yl)-1H-benzo[cd]indol-2-one

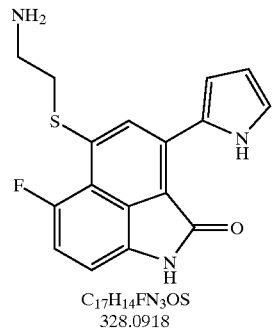

$C_{17}H_{14}FN_3OS$
328.0918

[2-[6-Fluoro-2-oxo-3-(1H-pyrrol-2-yl)-1,2-dihydro-benzo[cd]indol-5-ylsulfanyl]-ethyl]-carbamic acid tert-butyl ester (from Example 39 above) (30 mg) was dissolved at 0° C. in 50% TFA in $CH_2Cl_2$ solution (approximately 3 mL) that contained $H_2O$ (0.01 mL). After stirring for 2.5 hours the mixture was poured into ethyl acetate and extracted with aqueous ammonium hydroxide. The organic layer was dried over $Na_2SO_4$, filtered and evaporated to a yellow solid. This solid was purified by a precipitation out of THF with excess of pentane to give 5-(2-amino-ethanesulfanyl)-6-fluoro-3-(1H-pyrrol-2-yl)-1H-benzo[cd]indol-2-one as a yellow solid. (Yield 18 mg, 78%).

Example 41

5-(2-Amino-ethylsulfanyl)-6-fluoro-3-(1H-pyrrol-2-yl)-1H-benzo[cd]indol-2-one hydrochloride salt

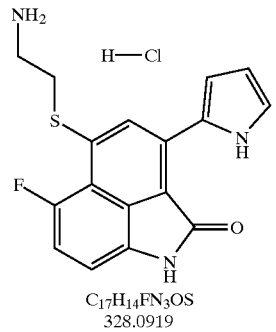

$C_{17}H_{14}FN_3OS$
328.0919

A solution of 5-(2-amino-ethylsulfanyl)-6-fluoro-3-(1H-pyrrol-2-yl)-1H-benzo[cd]indol-2-one (from Example 40 above) (20 mg, 0.06 mmol) in DMF (2.5 mL) was treated with aqueous HCl with vigorous stirring. The solution was lyophilized and the residue was dissolved in methanol, filtered and concentrated. The residue was further purified by precipitation out of methanol/CH$_2$Cl$_2$ (1:3) with excess pentane to give 5-(2-amino-ethylsulfanyl)-6-fluoro-3-(1H-pyrrol-2-yl)-1H-benzo[cd]indol-2-one hydrochloride salt as a dark yellow solid. (Yield 17 mg, 76%).

Example 42

5-(2-Amino-ethanesulfinyl)-6-fluoro-3-(1H-pyrrol-2-yl)-1H-benzo[cd]indol-2-one

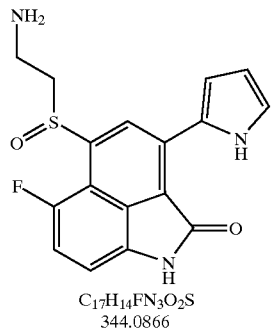

C$_{17}$H$_{14}$FN$_3$O$_2$S
344.0866

A solution of [2-[6-fluoro-2-oxo-3-(1H-pyrrol-2-yl)-1,2-dihydro-benzo[cd]indol-5-ylsulfanyl]-ethyl]-carbamic acid tert-butyl ester (from Example 39 above) (150 mg, 0.35 mmol) in THF (approximately 15 mL) was treated with mCPBA (Acros, 97 mg, 0.42 mmol, 75%) at 0° C. The reaction mixture was allowed to stir and warm up to room temperature overnight. The mixture was poured into ethyl acetate and washed successively with aqueous saturated Na$_2$S$_2$O$_3$ and aqueous saturated K$_2$CO$_3$. The organic layer was dried over Na$_2$SO$_4$, filtered, concentrated and the residue was purified by HPLC (silica gel, 40% ethyl acetate in hexanes). The resulting intermediate was precipitated out of THF with excess of pentane. This material was then dissolved at 0° C. in 50% TFA in CH$_2$Cl$_2$ solution (10 mL) that contained H$_2$O (0.5 mL) and stirred for 2 hours. Upon completion, the reaction mixture was diluted with ethyl acetate and extracted with aqueous ammonium hydroxide. The organic layer was dried over Na$_2$SO$_4$, filtered and concentrated to an orange solid. This solid was dissolved in THF and precipitated with excess of pentane to give 5-(2-amino-ethanesulfinyl)-6-fluoro-3-(1H-pyrrol-2-yl)-1H-benzo[cd]indol-2-one as an orange solid. (Yield 75 mg, 62%).

Example 43

5-(2-Amino-ethanesulfinyl)-6-fluoro-3-(1H-pyrrol-2-yl)-1H-benzo[cd]indol-2-one hydrochloride salt

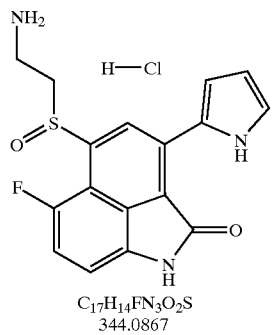

C$_{17}$H$_{14}$FN$_3$O$_2$S
344.0867

A solution of 5-(2-amino-ethanesulfinyl)-6-fluoro-3-(1H-pyrrol-2-yl)-1H-benzo[cd]indol-2-one (from Example 42 above) (20 mg, 0.06 mmol) in DMF (approximately 2.5 mL) was treated with aqueous HCl with vigorous stirring. The solution was lyophilized and the residue was dissolved in methanol, filtered and concentrated. The resulting material was further purified by precipitation out of MeOH/CH$_2$Cl$_2$ (3:1) with excess of pentane to give 5-(2-amino-ethanesulfinyl)-6-fluoro-3-(1H-pyrrol-2-yl)-1H-benzo[cd]indol-2-one hydrochloride salt as an orange solid. (Yield 19 mg, 77%).

Example 44

5-(2-Amino-ethanesulfonyl)-6-fluoro-3-(1H-pyrrol-2-yl)-1H-benzo[cd]indol-2-one

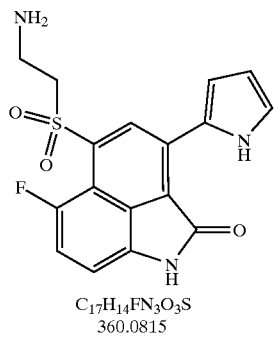

C$_{17}$H$_{14}$FN$_3$O$_3$S
360.0815

To a solution of [2-[6-fluoro-2-oxo-3-(1H-pyrrol-2-yl)-1,2-dihydro-benzo[cd]indol-5-ylsulfanyl]-ethyl]-carbamic acid tert-butyl ester (from Example 39 above) (100 mg) in THF (approximately 15 mL) was added solid K$_2$CO$_3$ (64 mg, 0.59 mmol). To this slurry was added mCPBA (Acros, 135 mg, 0.59 mmol, 75%) at room temperature. After 15 minutes at room temperature the reaction mixture was warmed to approximately 60° C. After stirring at 60° C. for 5.5 hours, the mixture was cooled and another portion of mCPBA (130 mg) was added. After stirring for an additional 16 hours at 60° C., another portion of mCPBA (260 mg) and K$_2$CO$_3$ (64 mg) were added. The reaction mixture was stirred for another 9 hours and a final portion of mCPBA (135 mg) was added. This mixture was stirred again overnight at 60° C. The reaction mixture was then diluted with EtOAc and washed with aqueous saturated Na$_2$S$_2$O$_3$ and aqueous saturated K$_2$CO$_3$. The organic layer was dried over Na$_2$SO$_4$, concentrated, and the residue was purified by HPLC (silica gel, 25% ethyl acetate in toluene) and precipitation out of THF with excess of pentane. The intermediate so obtained was dried and dissolved at 0° C. in a 50% TFA in CH$_2$Cl$_2$ solution (5 mL) that contained H$_2$O (0.2 mL). After 2 hours the reaction mixture was diluted with ethyl acetate and extracted with aqueous ammonium hydroxide and then with 5N NaOH. The pH of the aqueous layer was adjusted with concentrated HCl to 9 and then the ethyl acetate layer was separated, dried over Na$_2$SO$_4$, filtered and concentrated to dryness. The residue was further purified by precipitation out of THF with excess of pentane to give 5-(2-amino-ethanesulfonyl)-6-fluoro-3-(1H-pyrrol-2-yl)-1H-benzo[cd]indol-2-one as an orange-red solid. (Yield 8 mg, 1 0%).

Example 45

3,4-Dimethyl-2-(1-hydroxy-prop-2-ynyl)-pyrrole-1-carboxylic acid tert-butyl ester

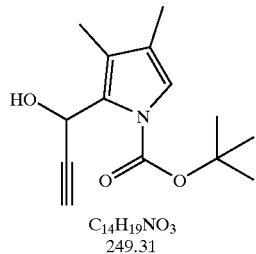

C$_{14}$H$_{19}$NO$_3$
249.31

To a solution of 3,4-dimethyl-2-formyl-pyrrole-1-carboxylic acid tert-butyl ester (3.18 g, 14.2 mmol) (prepared as described in Tietze et al., supra,) in dry THF(40 mL) was added ethynylmagnesium chloride (Aldrich, 0.5 M solution in THF, 57 mL, 28.5 mmol) dropwise at −65° C. and the reaction mixture was stirred at the same temperature for 0.5 hour. The cooling bath was then removed and the reaction mixture was stirred for another 2 hours to give a clear solution. The reaction was quenched by slowly adding EtOH (8 mL) and a saturated aqueous NH$_4$Cl solution (26 mL) at 5° C. The mixture was extracted several times with ethyl acetate. The combined organic extract was washed with brine, dried over anhydrous magnesium sulfate, filtered, and concentrated in vacuo. Flash chromatography (silica gel, 95:5 hexanes/ethyl acetate) purification of the crude oil afforded 3,4-dimethyl-2-(1-hydroxy-prop-2-ynyl)-pyrrole-1-carboxylic acid tert-butyl ester as a yellow oil. (Yield 3.54 g, 100.0%).

Example 46

2-tert-Butoxycarbonyloxy-4-[3-(1-tert-butoxycarbonyl-3,4-dimethyl-1H-pyrrol-2-yl)-3-hydroxy-prop-1-ynyl]-5-fluoro-indole-1-carboxylic acid tert-butyl ester

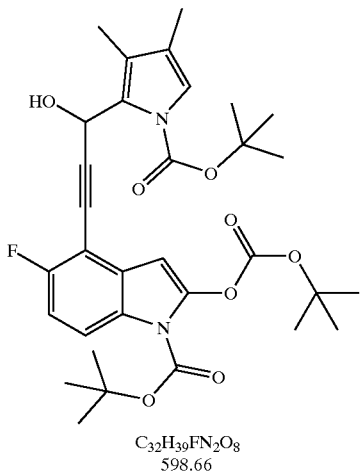

C$_{32}$H$_{39}$FN$_2$O$_8$
598.66

A solution of 2-tert-butoxycarbonyloxy-5-fluoro-4-iodo-indole-1-carboxylic acid tert-butyl ester (from Example 2 above) (1 g, 2.22 mmol), and 3,4-dimethyl-2-(1-hydroxy-prop-2-ynyl)-pyrrole-1-carboxylic acid tert-butyl ester (from Example 45 above) (1.38 g, 5.54 mmol) in dry THF(12 mL) and triethylamine(Aldrich, 12 mL) was degassed by bubbling argon through the solution for 10 minutes. At this time copper(I) iodide (Aldrich, 84.4 mg, 0.44 mmol) and (Ph$_3$P)$_4$Pd (0.25 g, 0.22 mmol) were added, and the reaction mixture was stirred at room temperature overnight. The reaction mixture was filtered and concentrated in vacuo. Flash chromatography (silica gel, 85:15 hexanes/ethyl acetate) afforded 2-tert-butoxycarbonyloxy-4-[3-(1-tert-butoxycarbonyl-3,4-dimethyl-1H-pyrrol-2-yl)-3-hydroxy-prop-1-ynyl]-5-fluoro-indole-1-carboxylic acid tert-butyl ester as an orange oil. (Yield 0.76 g, 57%).

Example 47

2-tert-Butoxycarbonyloxy-4-[3-(1-tert-butoxycarbonyl-3,4-dimethyl-1H-pyrrol-2-yl)-3-oxo-prop-1-ynyl]-5-fluoro-indole-1-carboxylic acid tert-butyl ester

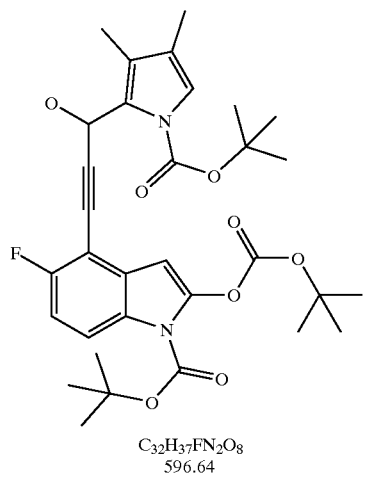

C$_{32}$H$_{37}$FN$_2$O$_8$
596.64

To a solution of 2-tert-butoxycarbonyloxy-4-[3-(1-tert-butoxycarbonyl-3,4-dimethyl-1H-pyrrol-2-yl)-3-hydroxy-prop-1-ynyl]-5-fluoro-indole-1-carboxylic acid tert-butyl ester (from Example 46 above) (0.76 g, 1.33 mmol) in CH$_2$Cl$_2$ (20 mL) was added MnO$_2$ (Aldrich, 1.36 g, 13.3 mmol) in one portion. The reaction mixture was stirred at room temperature for 24 hours. The reaction mixture was then filtered through Celiteo and the solid was washed with CH$_2$CO$_2$. The combined filtrates was concentrated in vacuo to give crude 2-tert-butoxy-carbonyloxy-4-[3-(1-tert-butoxycarbonyl-3,4-dimethyl-1H-pyrrol-2-yl)-3-oxo-prop-1-ynyl]-5-fluoro-indole-1-carboxylic acid tert-butyl ester as a brown solid which was used in the next step without further purification. (Yield 0.79 g, 100%).

Example 48

5-Fluoro-4-[1-iodo-3-oxo-3-(3,4-dimethyl-1H-pyrrol-2-yl)-propenyl]-1,3-dihydro-indol-2-one

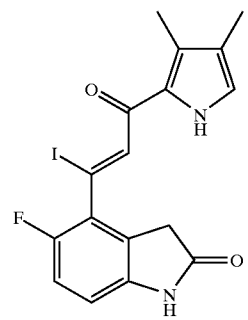

To a mixture of 2-tert-butoxycarbonyloxy-4-[3-(1-tert-butoxycarbonyl-3,4-dimethyl-1H-pyrrol-2-yl)-3-oxo-prop- 1-ynyl]-5-fluoro-indole-1-carboxylic acid tert-butyl ester (from Example 47 above) (0.79 g, 1.33 mmol) and sodium iodide (Aldrich, 0.50 g, 3.33 mmol) was slowly added TFA (Aldrich, 15 mL) at room temperature. The reaction mixture was stirred at room temperature for 1.5 hours, and then diluted with ethyl acetate and saturated aqueous sodium bicarbonate solution. After separation, the aqueous layer was extracted with ethyl acetate. The combined organic extracts were washed with brine, dried over anhydrous magnesium sulfate, filtered, and concentrated in vacuo. The crude product was triturated with ethyl acetate, filtered, and dried to give 5-fluoro-4-[1-iodo-3-oxo-3-(3,4-dimethyl-1H-pyrrol-2-yl)-propenyl]-1,3-dihydro-indol-2-one as a brown solid which was used in the next step without further purification. (Yield 0.40 g, 71.4%).

Example 49
[2-[6-Fluoro-2-oxo-3-(3,4dimethyl-1H-pyrrol-2-yl)-1,2-dihydro-benzo[cd]indol-5-ylsulfanyl]-ethyl]-arbamic acid tert-butyl ester

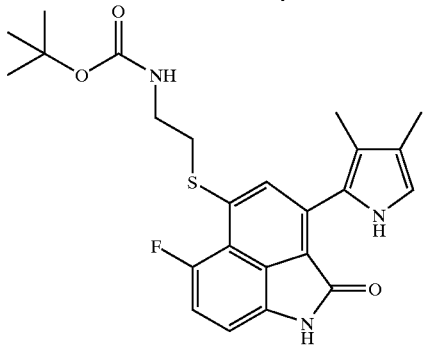

To a suspension of 5-fluoro-4-[1-iodo-3-oxo-3-(3,4-dimethyl-1H-pyrrol-2-yl)-propenyl]-1,3-dihydro-indol-2-one (from Example 48 above) (1.58 g, 4.0 mmol) in tert-butyl-N-(2-mercaptoethyl)-carbamate (Aldrich, 8 mL) was added NaH (Aldrich, 95%, 0.3 g, 11.8 mmol) in portions at room temperature. After stirring at room temperature for 30 minutes, the reaction mixture was heated to 120° C. for 3 hours. The reaction was quenched by adding brine and ethyl acetate. The organic layer was dried over anhydrous magnesium sulfate, filtered, and concentrated in vacuo. Purification of the residue by flash chromatography (silica gel, 4:1 hexanes/ethyl acetate) afforded [2-[6-fluoro-2-oxo-3-(3,4-dimethyl-1H-pyrrol-2-yl)-1,2-dihydro-benzo[cd]indol-5-ylsulfanyl]-ethyl]-carbamic acid tert-butyl ester as an orange oil. (Yield 66 mg, 31%).

Example 50
5-(2-Amino-ethylsulfanyl)-6-fluoro-3-(3,4-dimethyl-1H-pyrrol-2-y l)-1H-benzo[cd]indol-2-one trifluoroacetic acid salt

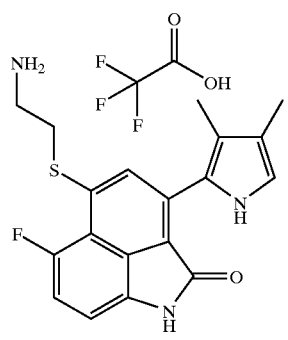

$C_{19}H_{18}FN_3OS$
356.1230

To a solution of [2-[6-fluoro-2-oxo-3-(3,4-dimethyl-1H-pyrrol-2-yl)-1,2-dihydro-benzo[cd]indol-5-ylsulfanyl]-ethyl]-carbamic acid tert-butyl ester (from Example 49 above) (66 mg, 0.145 mmol) in $CH_2Cl_2$ (5 mL) was added TFA (Aldrich, 2.5 mL) at 0° C. The mixture was stirred at 0° C. for 1 hour. Aqueous ammonium hydroxide (4 mL) and ethyl acetate were added. The aqueous phase was extracted with ethyl acetate. The ethyl acetate layers were combined and washed with brine, dried over anhydrous magnesium sulfate, filtered, and concentrated in vacuo. The residue was purified by RP-HPLC (C-18, eluted with 1% acetonitrile/0.05% TFA in $H_2O$) to give 5-(2-amino-ethylsulfanyl)-6-fluoro-3-(3,4-dimethyl-1H-pyrrol-2-yl)-1H-benzo[cd]indol-2-one trifluoroacetic acid salt as a yellow-green solid. (Yield 20 mg, 29.4%).

Example 51
(±)-cis-3-(tert-Butyl-dimethyl-silanyloxy)-cyclopentanol

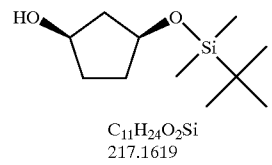

$C_{11}H_{24}O_2Si$
217.1619

To a solution of (±)-cis-tert-butyl-dimethyl-(6-oxa-bicyclo[3.1.0]hex-3-yloxy)-silane (prepared as described below) (2.15 g, 9.99 mmol) in EtOH (approximately 70 mL) was added 10% Pd/C (Aldrich, 500 mg). This mixture was hydrogenated with a Parr hydrogenator at 1 atmosphere pressure for 24 hours and then at 50 psi for another 24 hours. Upon completion of this time another portion of 10% Pd/C (500 mg) was added and the reaction mixture was hydrogenated for another 24 hours. Then the reaction mixture was filtered and the catalyst washed with THF. The combined organic layer was evaporated and the residue purified by flash chromatography (silica gel, 0–100% ether in hexanes gradient) to give (±)-cis-3-(tert-Butyl-dimethyl-silanyloxy)-cyclopentanol as a colorless oil. (Yield 1.81 g; 83%).

The (±)-cis-tert-butyl-dimethyl-(6-oxa-bicyclo[3.1.0] hex-3-yloxy)-silane starting material was prepared by standard tert-butyl-dimethylsilyl protection of (±)-cis-6-oxa-bicyclo[3.1.0]hexan-3-ol. (±)-cis-6-Oxa-bicyclo[3.1.0] hexan-3-ol was prepared according to Feeya, D. *J. Org. Chem.* 1981, 46, 3512–3519.

Example 52
(±)-trans-Thioacetic acid-[3-(tert-butyldimethyl-silanyloxy)-cyclopentyl]ester

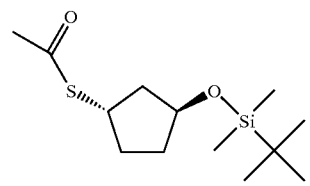

$C_{13}H_{26}O_2iS$
297.1318

To a solution of (±)-cis-3-(tert-butyl-dimethyl-silanyloxy)-cyclopentanol (from Example 51 above) (2.6 g, 12.02 mmol) and triphenyl phosphine (Aldrich, 7.9 g, 30.12 mmol) in dry THF (100 mL) at 0° C. was added dropwise diethyl azodicarboxylate (Aldrich, 4.8 mL, 30.48 mmol). After stirring for 15 minutes thioacetic acid (Aldrich, 2.2 mL, 30.78 mmol) was added dropwise. The reaction mixture was allowed to reach room temperature slowly and stirred overnight. Then, the reaction mixture was concentrated and the residue was purified by flash chromatography (silica gel, 0–5% ether in hexanes gradient) to give (±)-trans-thioacetic acid-[3-(tert-butyl-dimethyl-silanyloxy)-cyclopentyl]ester as a light yellow liquid. (Yield 2.36 g, 72%).

Example 53
(±)-5-[trans-3-(tert-Butyl-dimethyl-silanyloxy)-cyclopentylsulfanyl]-6-fluoro-3-(1H-pyrrol-2-yl)-1H-benzo[cd]indol-2-one

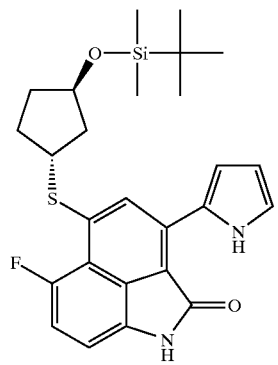

C$_{26}$H$_{31}$N$_2$O$_2$SiSF
483.1935

To a solution of (±)-trans-thioacetic acid-[3-(tert-butyl-dimethyl-silanyloxy)-cyclopentyl]ester (from Example 52 above) (2.4 g, 8.74 mmol) in methanol (60 mL) was added K$_2$CO$_3$ (1.45 g, 10.48 mmol) and the reaction mixture was stirred overnight. The reaction mixture was concentrated to a small volume and the residue was purified by flash chromatography (silica gel, 0–7% ether in hexanes to afford the corresponding unprotected thiol as a light yellow oil. To this intermediate was added (Z)-5-fluoro-4-[1-iodo-3-oxo-3-(1H-pyrrol-2-yl)-propenyl]-1,3-dihydro-indol-2-one (from Example 8 above) (150 mg, 0.30 mmol) and then NaH (110 mg, 4.53 mmol) in small portions at room temperature. After the evolution of hydrogen ceased, the reaction mixture was heated to 120° C. After 15 minutes at this temperature, DMF (0.1 mL) was added to facilitate dissolution and the reaction mixture was stirred for another 45 minutes at 120° C. Upon completion, the reaction mixture was diluted with ethyl acetate and H$_2$O. The H$_2$O layer was extracted with ethyl acetate (2×) and the combined organic layer was dried over Na$_2$SO$_4$ and concentrated. The residue was purified by HPLC (silica gel, 25% ethyl acetate in hexanes) to give (±)-5-[trans-3-(tert-butyl-dimethyl-silanyloxy)-cyclopentylsulfanyl]-6-fluoro-3-(1H-pyrrol-2-yl)-1H-benzo[cd]indol-2-one as a yellow solid. (Yield 7.8 mg, 5%).

Example 54
6-Fluoro-5-(-(S)-pyrrolidin-2-ylmethylsulfanyl)-3-(1H-pyrrol-2-yl)-1H-benzo[cd]indol-2-one

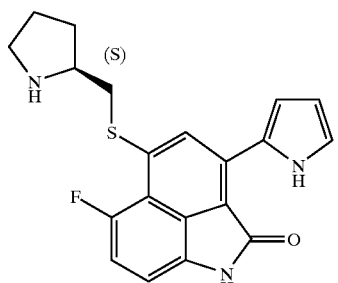

C$_{20}$H$_{18}$N$_3$OSF
368.1231

To (S)-N-Boc-thioprolinol (prepared as described below) (2.5 g, 11.50 mmol) was added (Z)-5-fluoro-4-[1-iodo-3-oxo-3-(1H-pyrrol-2-yl)-propenyl]-1,3-dihydro-indol-2-one (from Example 8 above) (150 mg, 0.302 mmol) and then NaH (110 mg, 4.53 mmol) in small portions. After the evolution of hydrogen ceased, the mixture was heated up to 120° C. for 1 hour and then cooled and partitioned between ethyl acetate and H$_2$O. The H$_2$O layer was washed again with ethyl acetate (2×). The combined organic layer was dried over Na$_2$SO$_4$, filtered, and concentrated. The resulting residue was purified by HPLC (silica gel, 30% ethyl acetate in hexanes), precipitated out of THF with excess of pentane, dried and dissolved in a 50% TFA in CH$_2$Cl$_2$ solution (6 mL) that contained H$_2$O (0.2 mL) at 0° C. After 2 hours this mixture was partitioned between ethyl acetate and aqueous 1N NaOH. The pH of the aqueous layer was adjusted to 14 with 1N NAOH and the aqueous layer was separated and extracted twice more with ethyl acetate. The combined organic layer was washed with H$_2$O (2×), dried over Na$_2$SO$_4$, and evaporated to dryness. This residue was purified by precipitation out of THF with excess of pentane to give 6-fluoro-5-(-(S)-pyrrolidin-2-ylmethylsulfanyl)-3-(1H-pyrrol-2-yl)-1H-benzo[cd]indol-2-one as a dark yellow solid. (Yield 45 mg, 41%).

S-N-Boc-thioprolinol was prepared according to Gilbertson, S. R.; Lopez, O. D. *J. Am. Chem Soc.* 1997, 119, 3399–3400.

Example 55
(S)-3-Mercapto-pyrrolidine-1-carboxylic acid tert-butyl ester

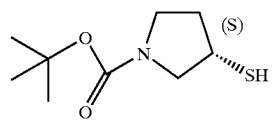

C$_9$H$_{17}$NO$_2$S
226.0874

A solution of N-tert-butyloxycarbonyl-(R)-(−)-pyrrolidinol (prepared as described below) (3.00 g, 16.04 mmol) and triphenylphosphine (Aldrich, 4.63 g, 17.64 mmol) in dry THF (70 mL) was treated at 0° C. with diethyl azodicarboxylate (3.07 g, 2.80 mL, 17.64 mmol). After 10 minutes, thioacetic acid (Aldrich, 1.34 g, 1.26 mL, 17.64 mmol) was added and the reaction mixture was allowed to warm up slowly to room temperature and stirred overnight. The reaction mixture was concentrated to a small volume and was purified by flash chromatography (silica gel, 0–30% ether in hexanes gradient). Fractions containing product were combined, and the solvents were evaporated and the resulting residue was treated with pentane and filtered. The pentane filtrate was evaporated to afford the desired intermediate thioacetic acid ester (2.24 g) which was immediately dissolved in methanol (60 mL). To this solution was added K$_2$CO$_3$ (1.5 g, 10.97 mmol) at room temperature and the reaction was stirred overnight. The reaction mixture was concentrated to a small volume and the residue was purified by flash chromatography (silica gel, 0–25% ethyl acetate in hexanes gradient) to give (S)-3-mercapto-pyrrolidine-1-carboxylic acid tert-butyl ester as a pale yellow liquid. (Yield 1.4 g; 38%).

The N-tert-butyloxycarbonyl-(R)-(−)-pyrrolidinol starting material was prepared according to Kucznierz, R; Grams, F.; Leinert, H.; Marzenell, K.; Engh, R. A.; von der Saal, W. J. Med. Chem. 1998, 41, 4983–4994.

Example 56

(S)-3-[6-Fluoro-2-oxo-3-(1H-pyrrol-2-yl)-1,2-dihydro-benzo[cd]indol-5-ylsulfanyl]-pyrrolidine-1-carboxylic acid tert-butyl ester

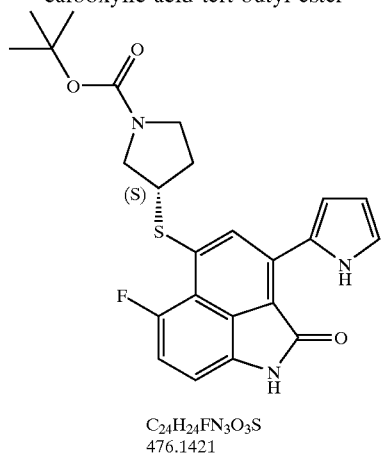

C$_{24}$H$_{24}$FN$_3$O$_3$S
476.1421

To a mixture of (S)-3-mercapto-pyrrolidine-1-carboxylic acid tert-butyl ester (from Example 55 above) (1.35 g, 5.81 mmol) and (Z)-5-fluoro-4-[1-iodo-3-oxo-3-(1H-pyrrol-2-yl)-propenyl]-1,3-dihydro-indol-2-one (from Example 8 above) (100 mg, 0.20 mmol) was added NaH (48 mg, 2.01 mmol) in small portions at room temperature. After the evolution of hydrogen ceased, the mixture was heated to 120° C. for 1 hour then cooled and partitioned between ethyl acetate and water. The water layer was extracted with ethyl acetate (3×) and the combined organic layer was dried over Na$_2$SO$_4$, filtered and concentrated. The residue was purified by HPLC (silica gel, 25% ethyl acetate in hexanes) followed by a precipitation out of THF with excess of pentane to give (S)-3-[6-fluoro-2-oxo-3-(1H-pyrrol-2-yl)-1,2-dihydro-benzo[cd]indol-5-ylsulfanyl]-pyrrolidine-1-carboxylic acid tert-butyl ester as a yellow solid. (Yield 57 mg; 62%).

Example 57

6-Fluoro-5-[(S)-(pyrrolidin-3-ylsulfanyl)]-3-(1H-pyrrol-2-yl)-1H-benzo[cd]indol-2-one

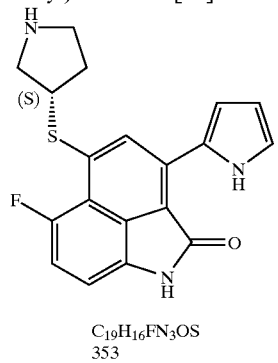

C$_{19}$H$_{16}$FN$_3$OS
353

(S)-3-[6-Fluoro-2-oxo-3-(1H-pyrrol-2-yl)-1,2-dihydro-benzo[cd]indol-5-ylsulfanyl]-pyrrolidine-1-carboxylic acid tert-butyl ester (from Example 56 above) (54 mg, 0.12 mmol) was dissolved at 0° C. in a 50% TFA in CH$_2$Cl$_2$ solution (6 mL) that contained H$_2$O (0.3 mL). After 2 hours the reaction mixture was partitioned between ethyl acetate and aqueous 1 N NaOH. The pH of the aqueous layer was adjusted to 14. The aqueous layer was extracted twice with ethyl acetate and the combined organic layer was washed with H$_2$O, dried over Na$_2$SO$_4$, filtered, and concentrated to dryness. The residue was purified by a precipitation out of THF with excess of pentane to give 6-fluoro-5-[(S)-(pyrrolidin-3-ylsulfanyl)]-3-(1H-pyrrol-2-yl)-1H-benzo[cd]indol-2-one as a yellow solid. (Yield 41 mg; 97%).

Example 58

Antiproliferative Activity

The antiproliferative activity of the compounds of the invention is demonstrated below. These activities indicate that the compounds of the present invention are useful in treating cancer, in particular solid tumors such as breast and colon tumors.

CDK2 FlashPlate Assay

To determine inhibition of CDK2 activity, purified recombinant retinoblastoma (Rb) protein was coated on 96 well FlashPlates (New England Nuclear, Boston, Mass.). Rb is a natural substrate for phosphorylation by CDK2 (Herwig and Strauss Eur. J. Biochem., Vol. 246 (1997) pp. 581–601 and references therein). Recombinant active human Cyclin E/CDK2 complexes were partially purified from extracts of insect cells. The active Cyclin E/CDK2 was added to the Rb-coated FlashPlates along with $^{33}$P-ATP and dilutions of test compounds. Plates were incubated for 25 minutes at room temperature with shaking, then washed and counted in the Topcount scintillation counter (Packard Instrument Co., Downers Grove, Ill.). Dilutions of test compounds were tested in duplicate in each assay. The percent inhibition of Rb phosphorylation, which is a measure of the inhibition of CDK2 activity, was determined according to the following formula:

$$100 \times \left[1 - \frac{\text{test compound} - \text{nonspecific}}{\text{total} - \text{nonspecific}}\right]$$

where "test compound" refers to the average counts per minute of the test duplicates, "nonspecific" refers to the average counts per minute when no Cyclin E/CDK2 was added, and "total" refers to the average counts per minute when no compound was added.

The results of the foregoing in vitro experiments are set forth in Table I below. The IC$_{50}$ value is the concentration of test compound that reduces by 50% the protein-kinase induced incorporation of the radiolabel under the test conditions described.

Each of the compounds in Table I had an IC$_{50}$ less than or equal to 1 0 μM.

TABLE I

| Example | CDK2 IC$_{50}$ (μM) |
|---------|---------------------|
| 7       | ≦10                 |
| 13      | ≦10                 |
| 6       | ≦10                 |
| 23      | ≦10                 |
| 16      | ≦10                 |
| 14      | ≦10                 |
| 9       | ≦10                 |
| 12      | ≦10                 |

TABLE I-continued

| Example | CDK2 IC$_{50}$ ($\mu$M) |
|---|---|
| 11 | ≦10 |
| 15 | ≦10 |
| 24 | ≦10 |
| 21 | ≦10 |
| 32 | ≦10 |
| 22 | ≦10 |
| 33 | ≦10 |
| 34 | ≦10 |
| 29 | ≦10 |
| 20 | ≦10 |
| 35 | ≦10 |
| 31 | ≦10 |
| 25 | ≦10 |
| 28 | ≦10 |
| 26 | ≦10 |
| 36 | ≦10 |
| 38 | ≦10 |
| 40 | ≦10 |
| 41 | ≦10 |
| 44 | ≦10 |
| 27 | ≦10 |
| 42 | ≦10 |
| 43 | ≦10 |
| 50 | ≦10 |
| 17 | ≦10 |

Cell-Based Assay (Tetrazolium Dye Proliferation Assay)

Proliferation was evaluated by the tetrazolium dye assay according to the procedure of Denizot abd Kabf (Denizot, F. and Lang, R. *J. Immunol Methods* 1986, 89, 271–277). The cell lines used were MDA-MB435, a breast carcinoma dell line and RKO, a colon carcinoma cell line.

Teh estrogen receptor negative epithelial breast carcinoma line (MDA-MB435) was purchased from American Type Cell Culture Collection (ATCC; Rockville, Md.) and was grown in the medium recommended by ATCC. For analysis of the test compounds on growth of these cells, the cells were plated at 2000 cells per well in a 96-well tissue culture plate, and were incubated overnight at 37° C. with 5% $CO_2$. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 $\mu$M. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below.

3-(4,5-Dimethylthiazole-2-yl)-2,5-diphenyl-2H-tetrazolium bromide (thiazolyl blue; MTT) was added to each well to yield a final concentration of 1 mglmL. The plates were then incubated at 37° C. for 3 hours. The plates were centrifuged at 1000 rpm for 5 minutes prior to aspiration of the MTT-containing medium. The MTT-containing medium was then removed and 100 $\mu$L 100% EtOH was added to each well to dissolve the resulting formazan metabolite. To ensure complete dissolution, plates were shaken for 15 minutes at room temperature. Absorbencies were read in a microliter plate reader (Molecular Dynamics) at a wavelength of 570 nm with a 650 nm reference. Percent inhibition was calculated by subtracting the absorbency of the blank (no cell) wells from all wells, then subtracting the division of the average absorbency of each test duplicate by the average of the controls from 1.00. Inhibitory concentrations (IC$_{50}$) were determined from the linear regression of a plot of the logarithm of the concentration versus the percent inhibition.

The colon carcinoma line RKO was also obtained from the ATCC and was tested according to the same protocol provided above except that the cell line RKO was plated at 500 cell per well.

The results of the foregoing in vitro tests are set forth below in Tables II and III. Each of the compounds in Tables II and III had an IC$_{50}$s less than or equal to 10 $\mu$M.

TABLE II

Antiproliferative Activity in Cell Line MDA-MB435*

| Example | MDA MB435 IC$_{50}$ ($\mu$M) |
|---|---|
| 7 | ≦10 |
| 13 | ≦10 |
| 6 | ≦10 |
| 23 | ≦10 |
| 16 | ≦10 |
| 9 | ≦10 |
| 12 | ≦10 |
| 11 | ≦10 |
| 15 | ≦10 |
| 24 | ≦10 |
| 21 | ≦10 |
| 32 | ≦10 |
| 22 | ≦10 |
| 33 | ≦10 |
| 34 | ≦10 |
| 19 | ≦10 |
| 35 | ≦10 |
| 36 | ≦10 |
| 38 | ≦10 |
| 40 | ≦10 |
| 41 | ≦10 |
| 44 | ≦10 |
| 42 | ≦10 |
| 43 | ≦10 |
| 50 | ≦10 |

Most of the data reflect the results of one experiment. In those cases where an experiment was repeated, the above data is an average of the results of the separate experiments.

TABLE III

Antiproliferative Activity in Cell Line RKO*

| Example | RKO IC$_{50}$ ($\mu$M) |
|---|---|
| 7 | ≦10 |
| 13 | ≦10 |
| 6 | ≦10 |
| 23 | ≦10 |
| 16 | ≦10 |
| 9 | ≦10 |
| 12 | ≦10 |
| 11 | ≦10 |
| 15 | ≦10 |
| 24 | ≦10 |
| 21 | ≦10 |
| 32 | ≦10 |
| 22 | ≦10 |
| 33 | ≦10 |
| 34 | ≦10 |
| 19 | ≦10 |
| 35 | ≦10 |
| 36 | ≦10 |
| 37 | ≦10 |
| 38 | ≦10 |

TABLE III-continued

Antiproliferative Activity in Cell Line RKO*

| Example | RKO IC$_{50}$ ($\mu$M) |
|---|---|
| 40 | ≦10 |
| 41 | ≦10 |
| 44 | ≦10 |
| 42 | ≦10 |
| 43 | ≦10 |
| 50 | ≦10 |

Most of the data reflect the results of one experiment. In those cases where an experiment was repeated, the above data is an average of the results of the separate experiments.

Example 59

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total weight | 120 | 120 | 150 | 300 | 600 | 900 |

*Compound A represents a compound of the invention.

Manufacturing Procedure

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 60

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure

1. Mix Items 1, 2 and 3 in a suitable mixer for 15 minutes.
2. Add Items 4 & 5 and mix for 3 minutes.
3. Fill into a suitable capsule.

Example 61

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | mL |

*Compound A represents a compound of the invention.

Manufacturing Procedure

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 µm filter and fill into vials.

Example 62

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 µm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula:

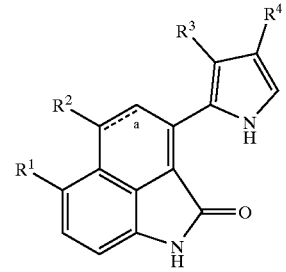

or the pharmaceutically acceptable salts or esters thereof, wherein:

$R^1$ is selected from the group consisting of
—H,
—$OR^5$,
halogen,
—CN,
—$NO_2$,
—$COR^5$,
—$COOR^5$,
—$CONR^5R^6$,
—$NR^5R^6$,
—$S(O)_nR^5$,
—$S(O)_2NR^5R^6$, and
lower alkyl which optionally may be substituted by $R^7$;

$R^2$ is selected from the group consisting of
—H,
—$OR^5$,
halogen,
—CN,
—$NO_2$,
—$COR^5$,
—$COOR^5$,
—$CONR^5R^6$,
—$NR^5R^6$,
—$S(O)_nR^5$,
—$S(O)_2NR^5R^6$,
lower alkyl which optionally may be substituted by $R^7$,
cycloalkyl which optionally may be substituted by $R^8$, and
heterocycle which optionally may be substituted by $R^8$;

$R^3$ and $R^4$ are each independently selected from the group of
—H,
—$OR^5$,
—CN,
—$NO_2$,
—$COR^5$,
—$COOR^5$,
—$CONR^5R^6$,
—$NR^5R^6$,
—$S(O)_nR^5$,
—$S(O)_2NR^5R^6$, and
lower alkyl which optionally may be substituted by $R^7$;

$R^5$ is selected from the group consisting of
—H
lower alkyl which optionally may be substituted by $R^7$,
cycloalkyl which optionally may be substituted by $R^8$,
aryl which optionally may be substituted by $R^8$,
heteroaryl which optionally may be substituted by $R^8$, and
heterocycle which optionally may be substituted by $R^8$;

$R^6$ is selected from the group of
—H
—$COR^9$,
—$CONR^9R^{10}$,
—$S(O)_nR^9$,
—$S(O)_2NR^9R^{10}$,
lower alkyl which optionally may be substituted by $R^7$, and
cycloalkyl which optionally may be substituted by $R^8$,
or, alternatively, $NR^5R^6$ optionally may form a morpholine, piperazine or piperidine ring, said ring being optionally substituted by $R^8$;

$R^7$ is selected from the group of
—$OR^9$,
halogen
—CN,
—$NO_2$,
—$COR^9$,
—$COOR^9$,
—$CONR^9R^{10}$,
—$NR^9R^{10}$,
—$S(O)_nR^9$,
—$S(O)_nNR^9R^{10}$;

$R^8$ is selected from the group of
—$OR^9$,
—CN,
=O,
—$NO_2$,
—$COR^9$,
—$COOR^9$,
—$CONR^9R^{10}$,
—$NR^9R^{10}$,
—$S(O)_nR^9$,
—$S(O)_2NR^9R^{10}$, and
lower alkyl which optionally may be substituted by $R^7$;

$R^9$ is selected from the group of
—H,
lower alkyl, and
cycloalkyl;

$R^{10}$ is selected from the group consisting of
—H,
—$COR_{11}$,
lower alkyl, and
cycloalkyl,
or, alternatively, $NR^9R^{10}$ optionally may form a morpholine, piperazine or piperidine ring;

$R^{11}$ is selected from the group consisting of
lower alkyl, and
cycloalkyl;

a is an optional bond; and
n is 0, 1 or 2.

2. The compound of claim 1, wherein, $R^1$ is selected from the group consisting of H, halogen, lower alkyl substituted by halogen, —$NO_2$, —$CONR^5R^6$, and —CN.

3. The compound of claim 2 wherein the lower alkyl substituted by halogen is perfluoroalkyl.

4. The compound of claim 3 wherein the perfluoroalkyl is —$CF_3$.

5. The compound of claim 1, wherein $R^2$ is selected from the group consisting of —H, —$OR^5$, —$NO_2$, —$CONR^5R^6$, —$S(O)_nR^5$ and lower alkyl which optionally may be substituted by $R^7$.

6. The compound of claim 2, wherein $R^2$ is selected from the group consisting of —H, —$OR^5$, —$NO_2$, —$CONR^5R^6$, —$S(O)_nR^5$, and lower alkyl which optionally may be substituted by $R^7$.

7. The compound of claim 6 wherein —$OR^5$ is selected from the group consisting of —$OCH_3$, —$OCH_2CH_3$, —$OCH_2CH_2OH$, —$OCH_2CH_2CH_2OH$, and —$OCH_2CH_2NH_2$.

8. The compound of claim 6 wherein the lower alkyl substituted by halogen is perfluoroalkyl.

9. The compound of claim 8 wherein the perfluoroalkyl is —$CF_3$.

10. The compound of claim 6 wherein $R^2$ is —$NR^5R^6$.

11. The compound of claim 10 wherein the —$NR^5R^6$ group is —$NHCH_2CH_2NH_2$.

12. The compound of claim 1 wherein $R^3$ is selected from the group consisting of H and lower alkyl which optionally may be substituted by $R^7$.

13. The compound of claim 6 wherein $R^3$ is selected from the group consisting of H and lower alkyl which optionally may be substituted by $R^7$.

14. The compound of claim 1 wherein $R^4$ is H.

15. The compound of claim 13 wherein $R^4$ is H.

16. The compound of claim 1 wherein $R^5$ is selected from the group consisting of lower alkyl which optionally may be substituted by $R^7$ and heterocycle which optionally may be substituted by $R^8$.

17. The compound of claim 15 wherein $R^5$ is selected from the group consisting of lower alkyl which optionally may be substituted by $R^7$ and heterocycle which optionally may be substituted by $R^8$.

18. The compound of claim 1 wherein Rs is lower alkyl which optionally may be substituted by $R^7$.

19. The compound of claim 17 wherein $R^6$ is lower alkyl which optionally may be substituted by $R^7$.

20. The compound of claim 1 wherein $R^7$ is selected from the group consisting of —$OR^9$ and —$NR^9R^{10}$.

21. The compound of claim 19 wherein $R^7$ is selected from the group consisting of —$OR^9$ and —$NR^9R^{10}$.

22. The compound of claim 1 wherein $R^8$ is selected from the group consisting of —$OR^9$ and —$NR^9R^{10}$.

23. The compound of claim 22, wherein $R^8$ is selected from the group consisting of —$OR^9$ and —$NR^9R^{10}$.

24. The compound of claim 1 wherein $R^9$ is selected from the group consisting of H and lower alkyl.

25. The compound of claim 24 wherein $R^9$ is selected from the group consisting of H and lower alkyl.

26. The compound of claim 1 wherein $R^{10}$ is selected from the group consisting of H and lower alkyl.

27. The compound of claim 26 wherein $R^{10}$ is selected from the group consisting of H and lower alkyl.

28. The compound of claim 1 wherein n is 0.

29. The compound of claim 28 wherein n is 0.

30. The compound of claim 1 wherein "a" is a bond.

31. The compound of claim 28 wherein "a" is a bond.

32. A compound of formula I selected from the group consisting of

6-Fluoro-5-morpholin-4-yl-3-(1H-pyrrol-2-yl)-1H-benzo[cd]indol-2-one, and

6-Fluoro-5-piperazin-1-yl-3-(1H-pyrrol-2-yl)-1H-benzo[cd]indol-2-one acetic acid salt, and the pharmaceutically acceptable salts or esters of the foregoing compounds.

33. A compound selected from the group consisting of

6-Fluoro-5-(4-hydroxy-piperidin-1-yl)-3-(1H-pyrrol-2-yl)-1H-benzo[cd]indol-2-one, 6-Fluoro-5-(3-hydroxymethyl-piperidin-1-yl)-3-(1H-pyrrol-2-yl)-1H-benzo[cd]indol-2-one, and 6-Fluoro-5-(3-hydroxy-piperidin-1-yl)-3-(1H-pyrrol-2-yl)-1H-benzo[cd]indol-2-one, and the pharmaceutically acceptable salts or esters of the foregoing compounds.

34. A pharmaceutical composition comprising as an active ingredient an effective amount of a compound of claim 1 and a pharmaceutically acceptable carrier or excipient.

35. The pharmaceutical composition of claim 34 which is suitable for parenteral administration.

* * * * *

UNITED STATES PATENT AND TRADEMARK OFFICE
CERTIFICATE OF CORRECTION

PATENT NO. : 6,531,598 B1
DATED : March 11, 2003
INVENTOR(S) : Apostolos Dermatakis, Jin-Jun Liu and Kin-Chun Luk It is certified that error appears in the above-identified patent and that said Letters Patent is hereby corrected as shown below:

Column 55,
Line 11, "Rs" should read -- $R^6$ --.

Signed and Sealed this

Nineteenth Day of August, 2003

JAMES E. ROGAN
*Director of the United States Patent and Trademark Office*